United States Patent [19]

Bobrov et al.

[11] 4,100,809

[45] Jul. 18, 1978

[54] METHOD FOR EXCITATION AND RECEPTION OF ULTRASONIC PLATE WAVES IN WORKPIECES AND DEVICES FOR REALIZING SAME

[76] Inventors: Vladimir Timofeevich Bobrov, ulitsa Zelinskogo 12, kv. 127; Jury Avraamovich Druzhaev, prospekt K. Marxa 2, kv. 19; Nelli Alexandrovna Lebedeva, ulitsa Kh. Livshits 29, kv. 25, all of Kishinev, U.S.S.R.

[21] Appl. No.: 708,263

[22] Filed: Jul. 23, 1976

[30] Foreign Application Priority Data

Jul. 28, 1975 [SU] U.S.S.R. ............... 2164385

[51] Int. Cl.² ........................................... G01N 29/04
[52] U.S. Cl. ....................................... 73/638; 73/643; 73/609
[58] Field of Search .......... 73/67.8 R, 67.8 S, 67.5 R, 73/67.7, 71.5 US, 638, 643, 609; 333/30 R; 310/8.1, 9.5; 324/37, 40

[56] References Cited

U.S. PATENT DOCUMENTS

| 3,436,958 | 4/1969 | Proctor | 73/67.7 |
|---|---|---|---|
| 3,786,672 | 1/1974 | Gaerttner | 73/67.5 R |
| 3,850,028 | 11/1974 | Thompson | 73/67.5 R |
| 3,869,683 | 3/1975 | Sokoloski | 333/30 R |
| 3,872,378 | 3/1975 | Shiraiwa et al. | 73/67.8 S |
| 3,919,669 | 11/1975 | Hartemann | 333/30 R |
| 3,964,296 | 6/1976 | Matzuk | 73/67.5 R |
| 3,975,698 | 8/1976 | Redman | 333/30 R |

FOREIGN PATENT DOCUMENTS

| 248,319 | 7/1969 | U.S.S.R. | 73/67.8 R |
|---|---|---|---|

OTHER PUBLICATIONS

Lockett, T. K.; "Lamb and Torsional Waves and Their Use in Flaw Detection", *Ultrasonics,* Jan. 1973, pp. 31–37.

*Primary Examiner*—Richard C. Queisser
*Assistant Examiner*—Stephen A. Kreitman

[57] ABSTRACT

A method and apparatus for excitation and reception of ultrasonic plate waves in a workpiece in which the surface of the workpiece is acted upon by a high-frequency electromagnetic field excited by a system of flat radiators forming a comb-shaped structure and positioned discretely in the direction of radiation with a pitch divisible by the wave length. A magnetizing field, whose vector is parallel to the surface of the workpiece under test, is introduced into the workpiece in the area of the high-frequency electromagnetic field and the vector of the magnetizing field is arranged at an angle relative to the radiation direction with respect to the flat radiator array to excite transverse normal waves.

21 Claims, 45 Drawing Figures

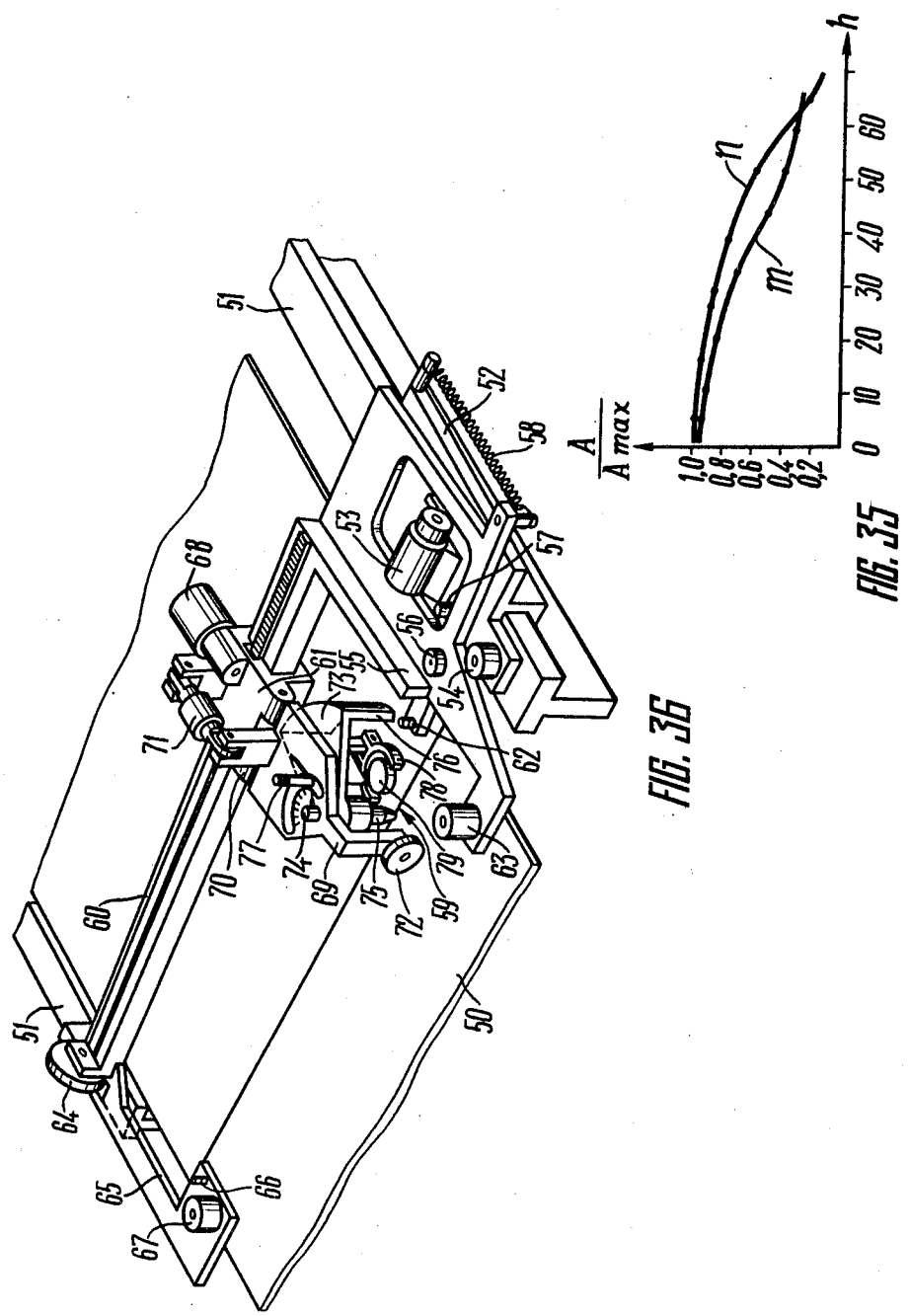

METHOD FOR EXCITATION AND RECEPTION OF ULTRASONIC PLATE WAVES IN WORKPIECES AND DEVICES FOR REALIZING SAME

FIELD OF THE INVENTION

This invention relates to ultrasonics and, in particular, to methods and devices for excitation and reception of ultrasonic plate waves in non-destructive testing of electrically conductive and ferromagnetic workpieces and in ultrasonic delay lines.

The invention can be used for non-destructive testing of ferromagnetic sheets, strips, pipes and other workpieces directly on production lines at a speed of up to 10 m/sec and more and with a higher reliability than currently used devices employing known methods of excitation and detection of ultrasonic plate waves by means of piezo-electric and "contactless" magnetoelectric acoustic transducers.

The invention can be also used in ultrasonics to produce waveguide ultrasonic delay lines, which in contrast to currently known ultrasonic delay lines ensure smooth adjustment of the delay, if an adequate number of branches is available, and permit transmission of signals without distortions caused by dispersion.

BACKGROUND

In the leading industrial countries, such as the USA, Great Britain, FRG, France and Japan, ultrasonic technology and methods of non-destructive testing have found extensive application. This can be attributed to the fast development of radio engineering and metallurgy, problems of miniaturization of computing equipment and high-speed apparatuses for quality testing of rolled stock.

In this connection extremely acute is the problem of providing such methods and devices for ultrasonic non-destructive testing as to increase testing efficiency, because employment of current methods and devices keeps the production process back and requires employment of apparatuses and expensive equipment outside the production process at some test zones.

Methods and devices should be developed to increase the reliability of testing, because the existing methods and devices, which require reliable acoustic contact between the radiator and the surface of the object under test, do not ensure reliable detection of flaws; demand more complicated electronic equipment and can discard workpieces with water drops, oil spots and other dirty patches on their surface. Workpieces with peeling scale cannot be tested at all.

Development of new methods and devices is also dictated by the necessity of increasing the sensitivity of testing, and non-destructive testing at high (over 100° C) and low (down to −50° C) temperatures of workpieces.

It is an important problem to provide methods and apparatuses ensuring development of ultrasonic delay lines with a smooth adjustment of the signal delay and an adequate number of tappings.

Methods and devices should be developed to produce dispersionless ultrasonic delay lines which ensure signal transmission without distortions.

At present there are known methods and apparatuses for generation and detection of ultrasonic plate waves, which are employed in ultrasonic engineering and, in particular, in ultrasonic inspection. They include methods and devices for excitation and detection of ultrasonic Lamb waves or longitudinal plate waves based on piezo-effect.

In these known methods and devices plate waves are generated and detected by inducing normal or tangential disturbances on the surface of a workpiece by means of piezoelectric transducers.

There are known several methods for exciting and detecting longitudinal plate waves (Lamb waves):
(1) by normal disturbances, induced by crystal or ceramic transducers uniformly in some area of the workpiece surface,
(2) by a combination of normal disturbances, distributed periodically over the surface of the workpiece and having a period equal to the length of the generated plate wave, the so-called "comb" array method,
(3) by normal disturbances, distributed according to the principle of a sine running wave over the surface of the workpiece — the "wedge" method.

All these methods are realized providing there is an acoustic contact of piezoelectric transducers with a workpiece. The first of the forementioned methods is practically not used because of its low efficiency and nonresonance nature (all possible types (modes) of plate waves at this frequency are generated in a workpiece). The "comb" method and the "wedge" method are resonance methods. The first permits excitation of a given mode by changing the distance between the teeth of the comb structure. The second permits such excitation by changing the angle of the piezoelectric transducer inclination with respect to the surface of the workpiece. The third of the discussed methods (the "wedge" method) has found application in ultrasonic engineering and in ultrasonic non-destructive testing.

Known devices realizing the "wedge" method comprise a piezoelectric transducer bonded to a prism made of perspex or organic glass and placed in a casing and a device ensuring acoustic contact with the surface of workpieces. When different types of waves are to be excited, a device is introduced for changing the inclination angle of the piezoelectric transducer with respect to the surface of the workpiece. In automatic inspection the device for excitation and reception of plate waves becomes much more complicated. Thus, automatic inspection of sheets in the production process at a speed of 5 m/sec is effected by means of a "wheel" contrivance containing the piezoelectrical transducer placed in a rubber wheel filled with the transformer oil. The device has many complicated parts, and oil is to be fed under the "wheel" in the process of testing to ensure acoustic contact.

In spite of wide application of the discussed methods and devices in ultrasonic flaw inspection, thickness gauging and testing the structure of the workpiece material, these methods and devices possess a number of serious drawbacks. Among them is the necessity of using coupling mediums and, consequently, dependence of the test results on the quality of acoustic contact and a low speed of inspection. Since water is most often used for acoustic contact, requirements to its purity are high, and the temperature of test objects is limited to the above-zero region, in particular it is kept between the freezing point 0° C and the boiling point 100° C, since steam upsets the acoustic contact. The use of adhesive for bonding the piezoelectric transducer to the prism can be the reason of quick failure of the device due to breaking of bonding, if the device operates in conditions of high environmental temperature.

And, finally, the presence of a normal component of the elastic vibrations displacement in the longitudinal plate wave results in reflected signals, which amplitude is comparable to that of signals caused by flaws of the object under test, if minute drops of water and oil stay on the surface of this test object. This leads to discarding fit workpieces and reduces reliability of inspection. Since practically all modes of longitudinal plate waves display dispersion (different components of the frequency spectrum propagate in a workpiece at different velocities and the pulse becomes wider, whereas its amplitude is additionally reduced), it is hard to use them for non-destructive testing. Modes are more effectively excited at the steep portions of dispersion curves of phase and group velocities, when piezoelectrical transducers are used, because the normal components of elastic vibrations displacement are great enough, but can be used only at small bases of sounding workpieces, because the influence of the dispersion sharply weaken and widen the pulses.

The duration of the pulse increases so that the untested edge of the sheet, which becomes the dead zone, can reach 0.2 m and more. The influence of dispersion is less at gently sloping portions of dispersion curves, but excitation of modes is ineffective due to small normal displacement components. At certain horizontal portions of dispersion curves of higher order modes signals cannot be excited at all by means of piezoelectric transducers. It is impossible to excite a zero antisymmetric mode of Lamb waves by the "wedge" method (with an organic glass prism).

All this results in more complicated techniques of selection of work points for flaw inspection and thickness gauging, more complicated and more expensive constructions of apparatuses, their worse technical characteristics and substantial losses in production.

There are known methods of excitation and reception of transverse (displacement) plate waves, which are also called SH-waves, by means of piezoelectric transducers:

1. by displacement disturbances, distributed uniformly over the surface of a workpiece in the band equal to the size of Y-cut crystal or piezoceramic transducers of respective polarization.

2. by a combination of displacement disturbances, distributed periodically over the surface of a workpiece with a space period equal to the length of excited transverse wave, that is the "comb" method.

Since transverse plate waves have no normal displacement components (displacements in transverse plate waves are parallel to surfaces of workpieces), devices for excitation and reception use piezoelectric transducers made of Y-cut crystal or piezoceramic plates of respective polarization. The acoustic contact between the piezoelectric transducer and the workpiece is achieved by bonding the transducer to the workpiece by means of viscous resins or similar substances (ceresine wax, etc.) which ensure transmission of displacing disturbances. This excludes employment of liquids as coupling mediums (water and the like), which does not permit employment of the discussed method for excitation and reception of transverse plate waves in motion, that is during relative movement of workpieces and devices for generation of such waves.

In this connection, at present transverse plate waves are not employed in ultrasonic flaw detection at all, but are used only in ultrasonic delay lines.

There are known a method and a device for generation and detection of Lamb waves (longitudinal plate waves), Rayleigh waves and others (cf. U.S. Pat. No. 3,850,028 Cl. 73/638) based on employment of "contactless" transducers and eliminating the drawbacks caused by the necessity of making an acoustic contact.

This method consists in that to generate and detect ultrasonic Lamb waves two separate transducers are used, each containing a serpentine conductor positioned parallel to the surface of the test object and in the field of a permanent magnet. Alternating current flowing in the conductor induces eddy currents in the test object, in directions transverse to the field of the permanent magnet. The interaction of eddy currents and the field of the permanent magnet result in elastic displacements, which are caused by Lorentz forces (ponderomotive forces) or magnetostriction. Since the serpentine conductor contains a number of parallel portions positioned across the magnetic field and the direction of currents in each parallel portion at any moment is opposite, Lamb waves are excited at the frequency, the product of which by the period (pitch) of the conductor coil is equal to the phase velocity of the elastic wave. In this case Lamb waves are emitted in two opposite directions perpendicular to the conductors.

A device for realization of the discussed method is a carriage mounted on wheels which are driven by a suitable motor mounted on the carriage to make the inspection device travel along a test object.

Two identical transducers mounted on the carriage in proximity with, but spaced from the test object, parallel to each other, one serving as a transmitter and the other as a receiver, are provided with a horseshoe-type permanent magnets, serpentine conductors being positioned between their poles. The carriage also mounts a power supply and a recorder to register the test results. In another embodiment of the device the test object and the serpentine conductor are placed between the poles of the permanent magnet.

But the discussed method and device possess a number of drawbacks related to the nature of Lamb waves and construction peculiarities. These drawbacks, dealt with in detail before, relate to poor reliability of testing because of the influence of minute drops of liquid and other dirt spots of the surface of the workpiece. Dispersion results in the fact that the use of separate transmitting and receiving transducers with an equal pitch (the distance between adjacent coil loops) impairs the test results, since the wave length and the pitch of the receiving transducer are determined disregarding the effect of dispersion on the parameters of the propagating wave. The discussed method and device do not ensure a signal reflected from flaws proportional to the size of these flaws. The method and device under discussion do not permit excitation and detection of transverse plate waves which possess certain advantages as compared to Lamb waves.

Besides, the device provided with separate transmitting and receiving transducers is almost twice more bulky and complicated in servicing, requires replacement of transducers and complete readjustment of equipment for measuring thickness of a test object, which makes its operation much more complex. The transducers, the permanent magnet, the supply source and the recorder placed on one carriage make it heavy which presents quite a problem when testing thin workpieces, deteriorate operating conditions of electronic units and the recorder, reduce the efficiency of testing.

There is also known a device for "contactless" generation and detection of transverse plate waves in testing workpieces (the USSR Author's Certificate No. 411,369 Cl. G01n/29/00, G01B 17/00) which is an electromagnetic acoustic tranducer comprising a magnet and an inductance coil made as a flat spiral and positioned between the test object and the magnet. To excite transverse plate waves the working butt of the magnet of the described device is made as a comb structure (alternating projections and depressions). The sensitivity is increased at the expense of a second comb structure made on the working butt of the magnet, the projections of one structure being in coincidence with the middles of depressions of the other structure). The coil is placed so that its one side is over one comb structure and the second side is over the other structure. The device ensures excitation of transverse plate waves in a workpiece without coupling mediums and at a great speed of movement of the workpiece.

But still, the device possesses some serious drawbacks. Among them are complicated construction of the device, the necessity of a large set of magnet pole shoes with different pitches of the comb structure, complicated adjustment of the device to a new thickness of a workpiece and its new surface shape, technological difficulties related to making pole shoes for excitation transverse plate waves in pipes of different diameters. Besides, resonance properties of the device sharply deteriorate, when testing workpieces made from ferromagnetic materials, which reduces the effectiveness of excitation of the required mode of normal waves.

Apart from the above described devices, there is known a device for generation of plate waves (cf. USSR Author's Certificate No. 375,546 Cl. G01n 29/04) comprising a casing, wherein an electromagnet is mounted. An inductance coil with evenly spaced sections is placed between the poles of the electromagnet. To increase sensitivity the inductance coil is made as a frame with curved slots, which are parts of a circle. The frame can be turned. The device increases sensitivity of testing due to focussing of ultrasonic vibrations.

The device's drawback consists in that the electromagnet and the inductance coil (frame) are arranged in one casing. This makes the transducer heavy, the access to the frame is difficult, when it needs to be replaced, and the transducer is bulky and inconvenient for testing thin-walled workpieces. The device does not permit optimal excitation of required modes of plate waves and optimal focusing conditions.

There is also known a method of excitation and detection of transverse plate waves in ultrasonic delay lines (cf. "Physical Acoustics" ed. Mason, Vol. 1, Methods and Devices for Ultrasonic Inspection, part A, Moscow, 1966, pp. 513). The ultrasonic delay line comprises a metallic band, which ends are bonded to piezoelectric transducers placed in perpendicular or inclined position with respect to its axis. The side surfaces of the band are insulated by a soundproof material. The piezoelectrical transducers are made of Y-cut crystal or piezoceramic plates of respective polarization. The discussed delay lines, which are called waveguide lines, have extensive application as memories in computers, for aircraft and navigational systems, in radio detection and ranging for pulse compression.

These devices are deficient in that it is impossible to smoothly adjust the delay time and create multi-branch delay lines.

SUMMARY OF THE INVENTION

It is an object of this invention to eliminate the above mentioned drawbacks of the known methods and devices for excitation and reception of ultrasonic normal waves.

Another object of this invention is to provide a method and a device for excitation and reception of ultrasonic plate waves to ensure not only a considerable rise in testing efficiency, as compared to known methods and devices, but an increase in reliability of testing and testing of workpieces at high temperatures, to simplify the design of the device, improve its operational characteristics, reduce expenditures on its production and operation by using transverse and longitudinal plate waves.

These objects are achieved in that in a method for excitation and reception of ultrasonic plate waves in workpieces, consisting in acting upon the workpiece surface by a high-frequency electromagnetic field excited by a system of flat radiators forming a comb-type structure and arranged discretely in the direction of the radiation with a pitch divisible by the wave length, introduction into the workpiece in the area of the high-frequency electromagnetic field of a magnetizing field, which vector is parallel to the surface of the test object, according to the invention, the vector of the magnetizing field is oriented at an angle to the radiation direction with respect to the flat radiator system to excite transverse (displacement) plate waves.

It is advisable, when exciting transverse plate waves in carbon steel workpieces, that the vector of the magnetizing field be oriented with respect to the flat radiator system at an angle of $\pm(10° \text{ to } 60°)$ to the radiation direction.

It is also advisable that, when plate waves are excited in workpieces made of non-retentive materials, the vector of the magnetizing field be oriented with respect to the flat radiator system at an angle of $\pm(20° \text{ to } 90°)$ to the radiation direction.

The employment of the proposed method permits excitation and reception of transverse plate waves and, consequently, greater speed and reliability of testing. Besides, transverse plate waves are excited and received by the proposed method in an easier way and no complicated readjustment is needed, which was inevitable in the known methods.

It is not unusual that different types of flaws are to be detected in workpieces (lamination, cracking, faulty fusion in welded joints) and different types of normal waves respond differently to such flaws. It is advisable, therefore, for simultaneous excitation and reception of pulses of transverse and longitudinal plate waves, that at least two excitation frequencies of the high-frequency electromagnetic field be selected, assuming the wave lengths of the transverse and longitudinal plate waves to be equal, according to the formula:

$$f_1 = (C_{x1}/\lambda_1); f_2 = (C_{x2}/\lambda_2)$$

where $C_{x1}$, $C_{x2}$ are phase velocities of the transverse and longitudinal normal waves respectively, $\lambda_1$, $\lambda_2$ are respective lengths of transverse and longitudinal waves, the pitch between the flat radiators being determined by means of the formula:

$$t = \lambda_1 = \lambda_2.$$

It is advisable that, for simultaneous excitation and reception of pulses of transverse and longitudinal normal waves with equal amplitudes on a specified test base, the vector of the magnetizing field be oriented with respect to the system of flat radiators at an angle of ±(5° to 40°) to the radiation direction.

The proposed method permits simultaneous excitation of longitudinal and transverse normal waves by means of one transducer. The method also permits obtaining equal amplitudes of pulses of different types of waves on a known (specified) test base. This is possible due to such selection of working excitation frequencies of the high-frequency electromagnetic field, in which the lengths of ultrasonic normal waves of different types become equal, thus ensuring their excitation and reception by one transducer, the pitch between radiators being divisible by the wave length. The angle between the vector of the magnetizing field and the direction of radiation in this case should be within the range of ±(5° to 40°).

It is advisable, that for simultaneous excitation and reception of pulses of the transverse and longitudinal waves being focussed in a specified point, the vector of the magnetizing field be oriented with respect to curved portions of flat radiators at an angle of ±(0° to 60°) to the direction of radiation.

Employment of the proposed method permits simultaneous optimal excitation and reception of transverse and longitudinal plate waves being focussed in a specified point and thus increase sensitivity of testing.

It is advisable that, for simultaneous excitation and reception of pulses of transverse and longitudinal waves, at least two excitation frequencies of high-frequency electromagnetic field be selected, assuming the lengths of the transverse and longitudinal plate waves to be equal, and the minimum test base be selected on condition that:

$$L \geq \frac{\tau}{2} \cdot \frac{C_{y\,max} \cdot C_{y\,min}}{C_{y\,max} - C_{y\,min}}$$

where $\tau$ is the duration of the detected high-frequency pulse, $C_{y\,max}$, $C_{y\,min}$ are group velocities of transverse and longitudinal plate waves.

If this condition is observed, distinct separation of pulses of different types of waves can be ensured at the specified base (width) of testing. Thus the reliability of testing is increased and deciphering of the test results becomes much simpler. This condition permits choice of modes of transverse and longitudinal plate waves with the maximum difference in group velocities, when testing workpieces with a narrow base (small width), which ensures decrease of the untested zone.

It is advisable that for excitation of a longitudinal plate wave (Lamb wave) being focused in a specified point, the vector of the magnetizing field be oriented with respect to the system of flat radiators, which are curved with radii equal to the distance to the focusing point and the length being equal to the effective width of the magnetizing field so that its direction coincides with the radiation direction.

Such method can be used for testing workpieces with similar flaws, which position is known in advance, e.g. for testing butt welds of pipes or strips. The method permits excitation of only one type (mode) of longitudinal plate waves, provides better conditions for focusing and thus increase sensitivity to flaws, which possible location is known in advance.

Taking into consideration the effect of dispersion in propagation of normal waves pulses and excluding the zero symmetrical mode of transverse waves SS(O), it is advisable that, with separate excitation and reception of plate waves, the pitch between flat radiators ensuring detection of normal waves be determined taking into account the influence of dispersion distortions on a specified test base by measuring the average wave length in a pulse of normal waves by superposition method.

The employment of the proposed method permits more effective testing, lets no flaw pass undetected, which can be due to the difference of wavelengths of generated pulses of ultrasonic vibrations and pulses received after they pass through the tested portion of the workpiece, which has not been taken into account in the known methods and devices.

The above mentioned objects are also achieved in that in a device for realization of the method for excitation and reception of ultrasonic plate waves in workpieces, comprising a system of flat radiators, which is a high-frequency transducer held against the workpiece surface by means of a spring-loaded leverage secured to a frame hinged on a lever mechanism featuring a lifting drive, and a magnetizing device placed coaxially with the high-frequency transducer, according to the invention, the high-frequency transducer is enclosed in a protective device mounted on the frame, which comprises at least two follow-up rollers positioned in one plane, having parallel axes and an elastic, electrically strong and mechanically durable ring band moving at the speed of the workpiece, the part of roller surface contacting the workpiece being coated with a layer of material ensuring its reliable coupling with the surface of the workpiece, the magnetizing device in this case can be turned in the plane parallel to the surface of the workpiece.

It is advisable that the magnetizing device be made as a solenoid, its axis being parallel to the surface of the workpiece, and a linkwork ensuring turning and fixing the solenoid in positions corresponding to excitation of required ultrasonic normal waves.

Employment of the proposed device ensures realization of the above discussed methods for excitation and reception of ultrasonic plate waves in testing workpieces at metallurgical works at higher testing speeds. The device permits effective excitation and reception of plate waves with considerable changes in the workpiece position with respect to both the magnetizing device and to the high-frequency transducer. The proposed design of the device has but a weak influence on the amplitude of the signal of ultrasonic normal waves, when the clearance between the test object and the magnetizing device varies. It ensures precise following of the surface of the workpiece by the high-frequency transducer by virtue of the leverage and maximum reduction of the device weight.

It is advisable, for testing the quality (flaw detection) of the butt weld of sheets or bands at the production line of a sheet mill, that an apparatus be used for excitation and reception of ultrasonic plate waves in workpieces, which device comprises a high-frequency transducer, which can rotate about the axis coinciding with the normal to the surface of the workpiece and is held against the workpiece surface by means of a leverage mounted on a magnetizing device featuring a lifting drive, said device being levered on a carriage having a drive for travelling on a guide placed across the test object and mounted on a platform, which can travel along the test object, said apparatus, according to the invention, being provided which at least two weld position sensors and two electromagnetic holds placed in pairs over the workpiece edges and mechanically connected to the high-frequency transducer by means of a guide ensuring the joint travel of the platform with the workpiece and of the high-frequency transducer along the tested weld by an electric drive.

It is advisable that the bracket of the guide be able to rotate and be spring-loaded in the direction of the test object movement and the platform be provided with an electromagnetic hold with respect to the longitudinal guide and return electric drives to bring the high-frequency transducer with the magnetizing device back to the initial position.

The proposed device is preferably used for excitation and reception of plate waves for testing the quality of welds of a sheet or a strip in the production line of a sheet mill. The device provides for testing a welded seam during movement of the sheet or strip by automatically registering the moment, when the welded seam is under the high-frequency transducer, and locking the device in a position ensuring precise specified distance between the welded seam and the high-frequency transducer, even if the line of the welded seam is skewed in relation to the sheet axis. Mose effective is a transducer, which ensures high sensitivity of testing by keeping the precise distance to the seam equal to the focal distance.

With appropriate adjustment the device ensures excitation of ultrasonic plate waves of different types. When the device is used together with the known electronic equipment (automatic apparatuses, recorders, etc.), it ensures a high degree of testing automation.

It is advisable that, for testing seamless and electrically welded pipes by ultrasonic plate waves, a device be employed to realize the method for excitation and reception of plate waves in workpieces, e.g. in pipes, comprising guide rollers mounted on a leverage, provided with a lifting drive, maintaining contact with the workpiece and carrying a magnetizing device, whereon at least two high-frequency transducers are placed and permanently pressed to the surface of the workpiece by a spring, said testing device, according to the invention, having the magnetizing device made as a sectionalized S-shaped magnetic circuit with at least three pole shoes, of which one immovable central pole shoe is detachable and two other adjustable pole shoes assembled of plates oriented according to the axis of the test object and moved along the S-shaped magnetic circuit by a screw pair, assuming by means of an adjustment and fixing unit the shape of the test object surface, whereas the high-frequency transducers positioned symmetrically with respect to the longitudinal axis of the S-shaped magnetic circuit travel along the surface by means of fork screw pairs and are secured in the fork so that they can rotate about the vertical axis in the plane parallel to the workpiece surface.

It is advisable that the adjustable pole shoes of the S-shaped magnetic circuit of the magnetizing device be able to rotate on levers about the hinges axis, which coincides with the axis of the S-shaped magnetic circuit.

It is advisable that the mount of the casing of the high-frequency transducer be made of a material with a low melting temperature and reproduce the shape of the test object surface by deformation, when heated.

The proposed device can be effective in excitation and reception of ultrasonic plate waves for testing the quality of seamless pipes, welded seams of straight-welded and spiral-welded pipes. In this case, depending on the test object and types of flaws, the device can excite longitudinal and transverse plate waves, or both types at a time. For this purpose the required conditions are provided by changing the position of adjustable pole shoes and the shape of the central pole shoe, as well as by selection of this or that high-frequency transducer (either focused or unfocused one). Inspection of a welded seam is to be done by means of focused high-frequency transducers. Inspection of the whole pipe body is more rationally done by non-focused transducers.

Owing to its diversity the design of the device ensures testing of pipes of a large variety of diameters. Introduction of the lifting-lowering drive of the device permits automatic testing in production lines for pipes manufacturing and trimming.

For testing the quality of seamless and electrically welded thin-walled pipes of a small diameter a device is preferably be used, comprising a magnetizing device with a high-frequency transducer mounted thereon by means of a spring-loaded leverage and provided with a lifting drive, wherein, according to the invention, the magnetizing device is made as a sectionalized U-shaped magnetic circuit with two pole shoes which can independently travel along and across the workpiece by means of screw drives and fixed in a specified position and the high-frequency transducer mounted on a leverage can travel along the workpiece and is provided with a frame secured on an elastic foundation, which assumes the shape of the test object surface when pressed thereto.

The proposed device is effective in testing pipes of a small diameter owing to the sectionalized magnetic circuit and interchangeable cone-shaped pole shoes ensuring with a simple readjustment inspection of pipes of various diameters. If pole shoes are set in the diameter plane of a pipe, the shifts of the pipe in this plane occurring in automatic testing have no influence on the test results. With different sizes of pole shoes different types of normal waves can be generated (longitudinal, transverse, focused and non-focused).

Since the high-frequency transducer is mounted on an elastic foundation, it assumes the shape of its surface, when pressed to the pipe. This increases sensitivity of testing and reduces the number of high-frequency transducers and the time required for their replacement.

To test workpieces of different thickness a device is preferably used for realization of the method for excitation and reception of plate waves, which comprises a magnetizing device with a high-frequency transducer mounted thereon by means of a rotating hand drive and made as a plate carrying a multi-link parallelogram mechanism with an adjustment drive and is provided, according to the invention, with discrete flat radiators made as sections mounted on the butts of L-shaped plates and assembled as a pack in casings, each plate being connected to the joints of respective links of the parallelogram mechanism.

Employment of the device with an adjustable pitch permits quick readjustment of equipment to comply with a different thickness of test objects, as well as selection of the required work point on dispersion curves.

To adjust the pulse delay time an ultrasonic delay line is preferably used realizing the method for excitation and detection of transverse normal waves and comprising an acoustic guide made as a band section with side edges insulated by sound-proof material, a radiator being installed at its one end and the straight portion of the other end carrying a magnetizing device with a detection transducer, wherein, according to the invention, the band of the acoustic guide is made of a ferromagnetic material and the detection transducer is made as a high-frequency transducer placed together with the magnetizing device into a housing provided with a screw drive to move it along the straight portion of the acoustic drive.

The band ultrasonic line permits smooth adjustment of the pulse delay time.

To delay one pulse for different time it is advisable that an ultrasonic delay line be used, which, according to the invention, comprises several receiving ultrasonic transducers with magnetizing devices provided with drives to move it along the acoustic guide.

BRIEF DESCRIPTION OF THE DRAWINGS

The invention will now be described in more detail with reference to several embodiments thereof, taken in conjunction with the accompanying drawings, wherein:

FIG. 35 shows the dependence of the amplitude of transverse plate waves signals on the clearance between the test object and pole shoes of the magnetizing device and between the test object and the surface of the solenoid;

FIG. 36 shows a device for inspection of a butt welded seam;

DETAILED DESCRIPTION

Figure 1:
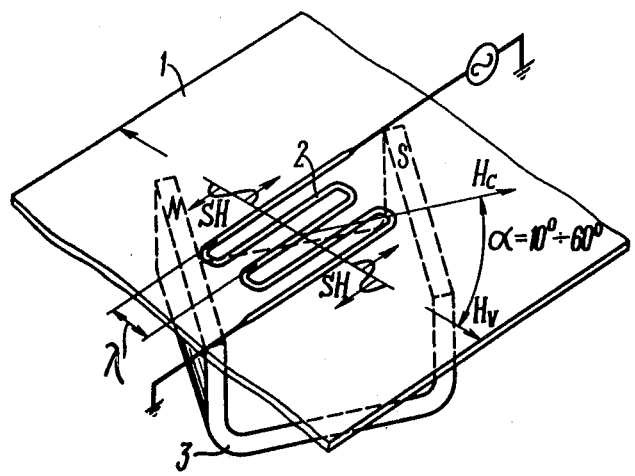
FIG. 1 shows interaction of a system of flat discrete radiators, the test object and the magnetizing field when transverse SH plate waves are excited.

A number of specific terms is used in the description which can be defined as follows.

Mode is a type of a plate wave propagating in the workpiece made as a solid plate (layer) with free boundaries at a definite ratio of the wave length and the thickness of the plate. There exist symmetrical and antisymmetrical modes of the zero, first, second "n-th" order.

Symmetrical mode is a normal wave wherein movement is symmetrical with respect to the plane positioned in the middle of the plate (that is the tangential displacements in the upper and lower halves of the plate are of the same sign, whereas the normal displacement has opposite signs).

Antisymmetrical mode is a normal wave, wherein movement is antisymmetrical with respect to the plane positioned in the middle of the plate (that is, in the upper and lower halves of the plate the tangential displacement has opposite signs and the normal displacement has the same signs).

Phase velocity is the velocity of propagation of a phase of harmonic (sine) waves:

$$C_x = f\lambda = \lambda/T$$

where
$C_x$ — phase velocity,
$f$ — frequency of harmonic vibrations,
$\lambda$ — wave length,
$T$ — period of vibrations.

The phase is determined by the instantaneous value and direction of the displacement of a vibrating particle. If particles are in a similar position with respect to the equilibrium state at a certain moment, they are said to be vibrating "in phase". The distance between two nearest particles vibrating in phase taken along the direction of propagation is the wave length ($\lambda$). The period of vibration (T) is the time during which the particle completes the total vibration cycle.

Group velocity is the velocity of a group of harmonic waves (modulated vibrations). For normal waves the group velocity is determined as:

$$C_y = C_x - \lambda(dC_x/d\lambda)$$

Dispersion is the dependence of velocity on the frequency of vibrations.

Dispersion distortions are changes of duration, frequency and amplitude of a pulse owing to the dependence of the velocity on the frequency of vibrations.

Comb method is a method of excitation of plate waves producing a periodic combination of normal or displacing disturbances with a space period $\lambda$ on the surface of the plate.

Wedge method is a method of excitation of plate waves based on transformation of longitudinal waves into plate waves. A longitudinal wave falls upon the surface of a plate of liquid or a solid prism made of organic glass at an angle $\theta$. The maximum excitation condition is $\sin\theta = C_z/C_x$, where $C_z$ is the velocity of a longitudinal wave in a liquid or prism and $C_x$ is the phase velocity of a normal wave.

Magnetostriction is a change of dimensions (deformation) of ferromagnetic bodies in the magnetic field. The magneto-striction effect ensures excitation of ultrasonic vibrations in ferromagnetic bodies acted upon by the high-frequency electromagnetic field.

The quadratic magnetostrictive effect can be linearized by the permanent magnetic field and the matter will consequently display a piezomagnetic effect. An external magnetizing field orients, depending on its force, elementary magnets of a ferromagnetic body in a more or less uniform direction and the body start acting like a piezomagnetic, similar to a single crystal.

Lorentz force (or ponderomotive force) is the forced $\vec{F}$ acting on the charge "e" moving in the magnetic field $$\vec{F} = \frac{e}{c}(\vec{V} \times \vec{H})$$

where V is the velocity of the charge "e".

H is the strength of the magnetic field where this charge moves, values being taken in each point for that point only.

Superposition method is addition of signals by matching in time for measuring the wave length.

Echo pulse method of flaw detection is a method of detecting flaws by means of a signal (echo signal) reflected from a flaw.

Through transmission method of flaw detection is a method of flaw detection by attenuation of a signal (through signal) after it has passed through the test portion of a workpiece.

A method of excitation and reception of ultrasonic transverse plate waves consists in acting on the surface of a test object 1 (e.g. a sheet in FIG. 1) by a high-frequency electromagnetic field generated by a system of flat radiators 2 forming a comb-shaped structure and positioned discretely in the direction of radiation with a pitch divisible by the wave length $\lambda$. A magnetizing field is introduced into the workpiece 1 in the area of the high-frequency electromagnetic field whose vector Hc is parallel to the surface of the test object 1. In this case the magnetizing field can be obtained by means of a permanent magnet 3 or an electromagnet ensuring permanent, low-frequency or pulsed magnetizing field.

To excite transverse plate waves the vector Hc of the magnetizing field is oriented with respect to the flat radiators 2 at an angle of $\pm\alpha$ relative to the direction of radiation, which coincides to the normal to the system of the flat radiators 2. This is achieved by turning the permanent magnet 3 respectively in the plane parallel to the surface of the test object 1.

In this case, depending on the ratio between the frequency f of the high-frequency electromagnetic field, the thickness d of the test object 1 and the pitch of the flat radiator system 2 this or that mode of transverse plate waves is excited. Such dependence for workpieces made of a material with certain elastic properties is presented as dispersion curves of phase velocities (solid lines) and group velocities (dashed lines) of transverse normal waves (FIG. 2), where the product of the frequency of the electromagnetic field f by the thickness of the test object d is plotted along the horizontal axis and the magnitude of the phase and group velocities is plotted along the vertical axis.

Figure 2:
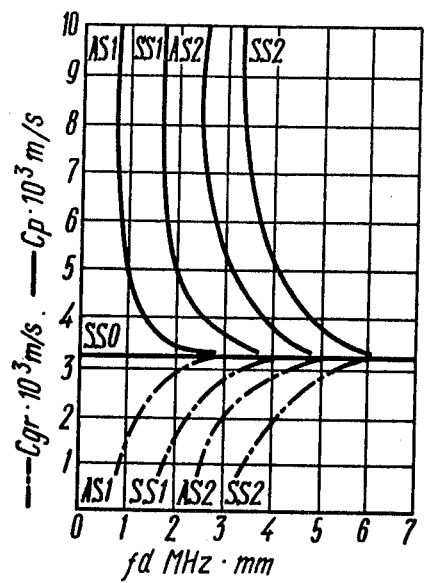
FIG. 2 shows dispersion curves of phase and group velocities of transverse normal waves.

Referring to FIG. 2, the zero symmetrical mode of transverse plate waves SS(0) has no dispersion and the magnitudes of the phase and group velocities coincide, whereas their dependence on the product $f \cdot d$ is represented by a horizontal line. This mode, as it has already been mentioned, offers considerable advantages when used in ultrasonic flaw detection, because propagation of even very short pulses of this mode brings about no changes in its shape and no additional attenuation due to dispersion. This ensures higher resolution and efficiency of testing of workpieces and permits testing workpieces of various thickness without readjustment of the device and replacement of transducers.

Symmetrical and antisymmetrical modes of higher orders ($SS_1$, $SS_2$, $AS_1$, $AS_2$) possess dispersion.

Ultrasonic transverse plate waves excited in the above described interaction have no displacement components normal to the surface of the test object 1 (FIG. 1). That is why their employment ensures testing of objects with drops of liquid, oil, completely or partially immersed in liquid, or pipes with liquid or high temperature liquid mediums flowing therein.

Transverse plate waves insure more proportional dependence of the amplitude of a pulse on the depth of the flaw. But they could not be used for non-destructive testing because they cannot be excited and received by piezoelectric transducers, when workpieces are in movement (dynamically).

Transmission of elastic wave pulses without dispersion distortions is also used in ultrasonics in non-dispersion ultrasonic delay lines. But the known band ultrasonic delay lines are made discrete only, rated for definite durations. Employment of the proposed method permits development of multichannel adjustable ultrasonic band delay lines with smoothly regulated delay. It is essential that the capacity of such delay lines is twice that of delay lines, wherein the zero symmetrical longitudinal mode in the low disperison zone is used, because the group velocity of this mode (FIG. 2) is half that of the zero symmetrical mode of Lamb waves. This permits reduction of the length and dimensions of the delay line.

It should be noted that the excited wave is radiated in two opposite directions normal to the flat radiators.

Figure 3:
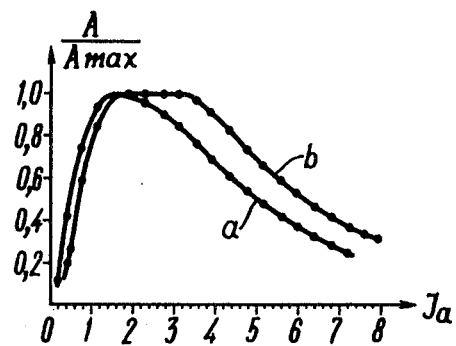
FIG. 3 shows the dependence of the amplitude of transverse plate waves signals on the magnetization of the workpiece (the magnetization current of the magnetizing device solenoid)

The advantage of the proposed method for excitation and reception of transverse plate waves consists in that all phenomena take place in a weak magnetizing field. With a certain magnetization the dependence of the amplitude of signals of transverse plate waves upon the magnetization of the workpiece (magnetization current) reaches its maximum. (FIG. 3). For workpieces of different thickness this dependence is different. It becomes sharper for thin sheets, e.g. the curve "$a$" represents the sheet thickness of 0.5 mm, and more smooth as the thickness increases, the curve "$b$" represents the sheet thickness of 1.0 mm. The nature of this dependence is to a certain degree associated with the shape of the magnetic circuit of a magnet (or electromagnet). The dependence in question allows for concluding that the basis of interactions providing for excitation and reception of ultrasonic transverse waves is the magnetostriction effect. Moreover, when magnetostrictional interactions take place in the presence of a magnetizing field, the frequencies of elastic and high-frequency vibrations coincide and phenomena during excitation and reception of ultrasonic waves are reversible, that is piezomagnetic transformation takes place. Certain role in this case is played by pondermotive interactions (Lorentz forces effect).

Figure 4:
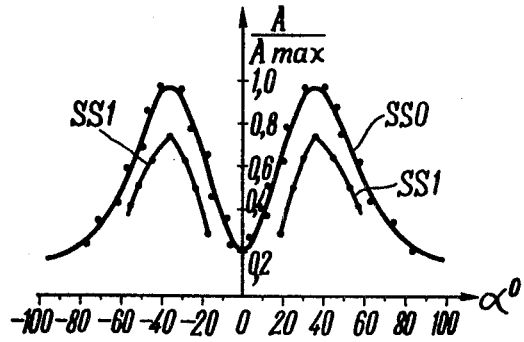
FIG. 4 shows the dependence of the amplitude of a transverse normal wave on the angle between the vector of the magnetization field and the direction of radiation.

When conditions of excitation of this or that mode of transverse plate waves are observed in accordance with the dependencies of FIG. 2, optimum excitation of this mode is not ensured. This is achieved by selection of an angle $\alpha$ between the vector of the magnetizing field and the direction of radiation in accordance with the dependencies of FIG. 4, where the value of angle $\alpha$ is plotted along the horizontal axis, whereas relative values of amplitudes of pulses of transverse plate waves of two symmetrical modes: zero mode SS(0) and first mode SS(1), are plotted along the vertical axis. Referring to FIG. 4, these dependencies are at their maximum with a certain value of the angle $\alpha$. These optimum angles for excitation of different modes in different materials (of different magnetic properties) are different (36°, 45°, etc).

In excitation of transverse plate waves in the test object 1 made of carbon steel the angle $\alpha$ is proposed to be within the range of ±(10° to 60°).

Figure 5:
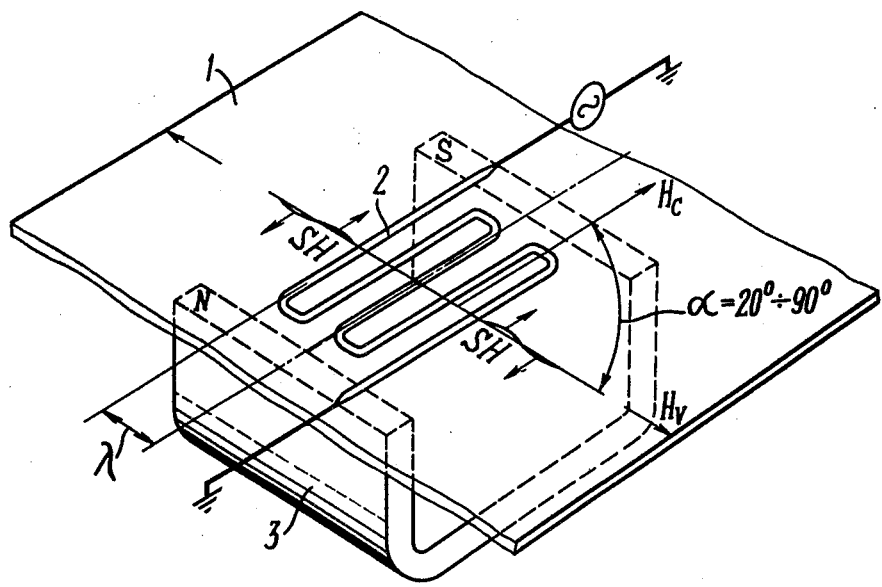
FIG. 5 explains interaction of a system of flat discrete radiators, the workpiece made of a non-retentive material and the magnetizing field, when plate waves are excited.
Figure 6:
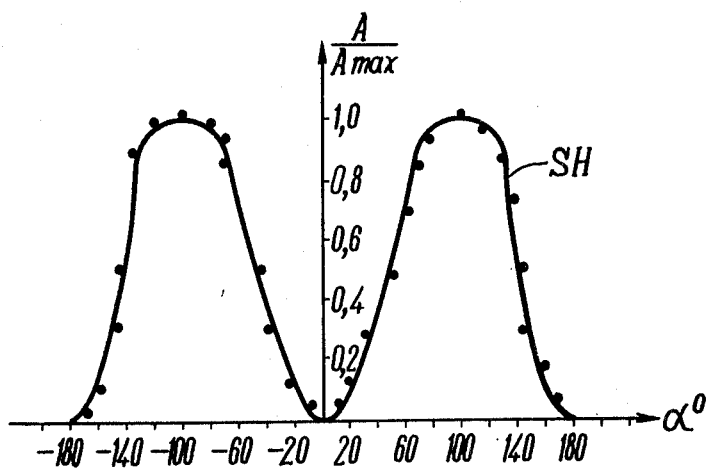
FIG. 6 shows the dependence of the amplitude of a plate wave pulse on the angle between the vector of the magnetizing field and the direction of radiation for non-retentive materials.

For excitation of plate waves in the test object 1 (FIG. 5) made of non-retentive material (e.g. permalloy) optimum angles between the direction of the vector of the magnetizing field and the direction of radiation lie within the range of (20° to 90°) (FIG. 6).

In practical flaw detection it is not rare, when flaws of different types are to be found in a workpiece (laminations, cracks, incomplete fusion in welded seams of bands. pipes, etc.). Since reliable detection of such flaws is only possible when different types of ultrasonic plate waves are used, a problem arises of simultaneous excitation longitudinal (Lamb) waves and transverse (SH) plate waves, the first being better for laminations and the second for cracks and incomplete fusions in welded seams.

In this connection, there is proposed a method for simultaneous excitation and reception of pulses of transverse and longitudinal plate waves, which consists in acting on the surface of the test object 1 (FIG. 7) by a high-frequency electromagnetic field generated by a system of flat radiators 2 forming a comb-shaped structure and arranged discretely in the direction of radiation with a pitch equal to the wave length $\lambda$. A magnetizing field is introduced into the workpiece in the zone of the high-frequency electromagnetic field, whose vector Hc is parallel to the surface of the test object 1. In this case the magnetizing field can be induced by means of a permanent magnet 3 or an electromagnet ensuring permanent low-frequency or pulsed magnetizing field.

The above described magnetostrictional phenomena are also the basis of the physics of the process taking place during simultaneous excitation of longitudinal and transverse plate waves. That means that elastic disturbances are the result of interaction of the induced high-frequency electromagnetic field and the magnetizing field, which can be permanent, low-frequency or pulsed field, said disturbances possessing displacement components, when transverse plate waves are excited, and plate and tangential (longitudinal) components, when exciting longitudinal plate waves. For simultaneous excitation of two types of plate waves, at least two frequencies for excitation of a high-frequency electromagnetic field are selected according to the following formula:

$$f_1 = (C_{x1}/\lambda_1); f_2 = (C_{x2}/\lambda_2)$$

where $C_{x1}$, $C_{x2}$ are phase velocities of respectively the transverse and longitudinal plate waves, $\lambda_1$, $\lambda_2$ are lengths of respectively the transverse and longitudinal plate waves.

The pitch between flat radiators $$t = \lambda_1 = \lambda_2$$

Figure 7:
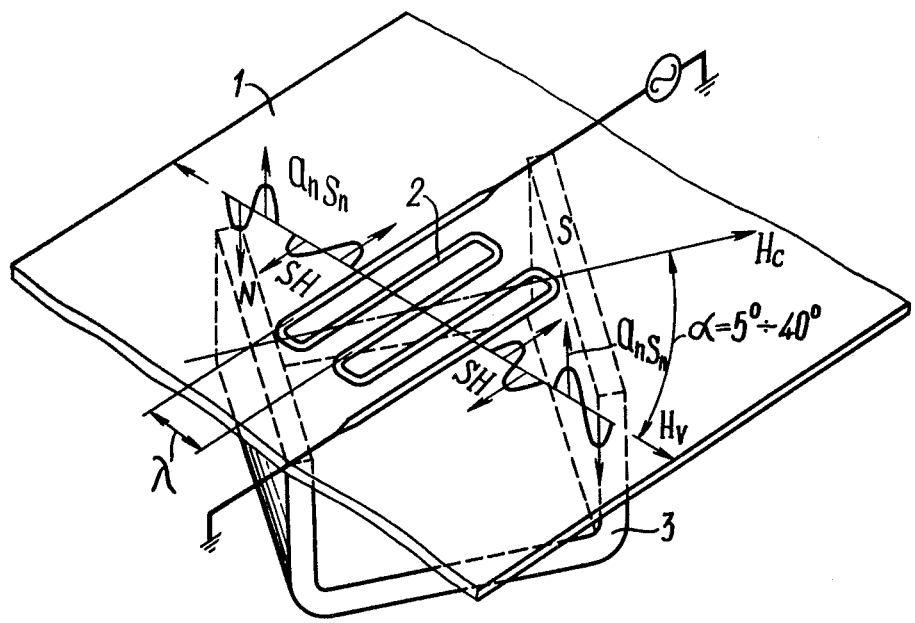
FIG. 7 explains interaction of a system of flat discrete radiators, the test object and the magnetizing field when longitudinal $A_n S_n$ and transverse SH plate waves are simultaneously excited and detected.

When the above mentioned conditions are observed, longitudinal ($A_n$, $S_n$) and transverse (SH) plate waves are excited in the test object 1 (FIG. 7). They are of respective modes, which are determined by the diagrams (FIG. 2) of dispersion curves of transverse plate waves and longitudinal plate waves (Lamb waves) (FIG. 8).

Figure 8:
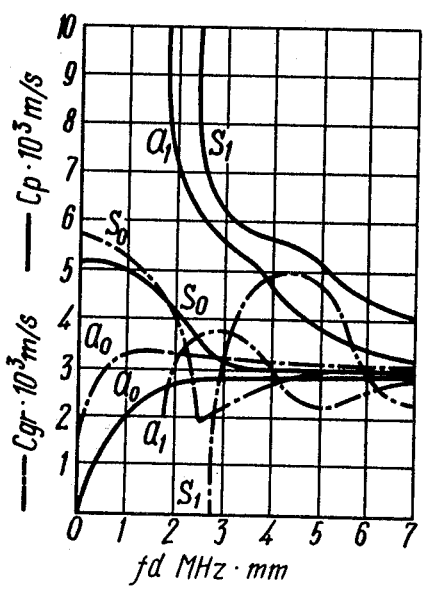
FIG. 8 shows dispersion curves of phase and group velocities of longitudinal plate waves in plates.

As the comparison of the diagrams of FIG. 2 and FIG. 8 indicates, even the zero modes of symmetrical and antisymmetrical longitudinal plate waves ($A_o$, $S_o$ of FIG. 8) possess certain dispersion. It becomes more evident for modes of higher orders ($A_1$, $S_1$).

Unlike the dispersion curves of transverse normal waves (FIG. 2) where group velocities (indicated by a dot-dash line) are always less or equal to the shear wave velocity, group velocities of longitudinal plate waves (indicated in FIG. 8 by a dot-dash line) can be in excess of the shear wave velocity.

The angle $\alpha$ between the vector of the magnetizing field and the direction of radiation is selected in accordance with the dependencies of amplitudes of longitudinal waves ($A_o$, $S_o$ modes) and transverse plate waves ($SS_o$, $SS_1$) on this angle (FIG. 9) to obtain pulses of different types of waves with a similar amplitude at a specified test base.

Figure 9:
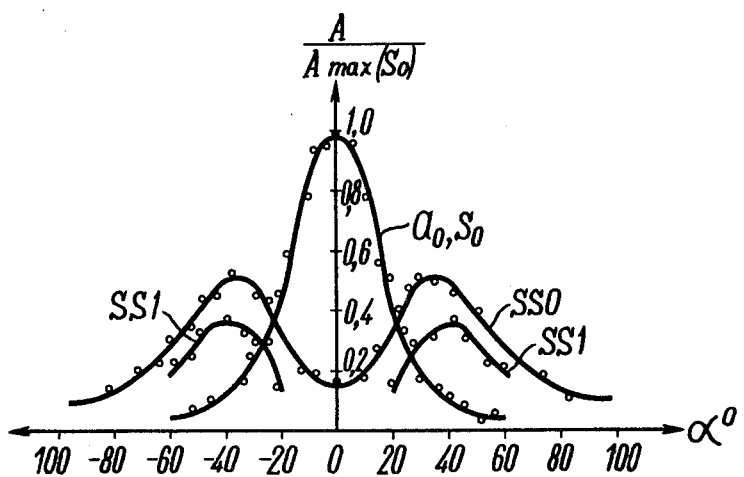
FIG. 9 shows the dependence of the amplitude of longitudinal ($A_o$, $S_o$ modes) and transverse (SS(0), SS(1) modes) plate waves on the angle between the vector of the magnetizing field and the direction of radiation.

As the diagrams of FIG. 9 indicate, these characteristics are at their maximum with different values of the angle $\alpha$($A_o$, $S_o$ modes of longitudinal plate waves are optimally excited at $\alpha = 0$, $SS_o$ and $SS_1$ modes, as it has been shown before, are optimally excited at $\alpha = 40°$–45°). For simultaneous excitation of longitudinal and transverse plate waves in carbon steel plates the angle $\alpha$ is selected within the range from 5° to 40° depending on the required ratio of pulses of said waves.

Figure 10:
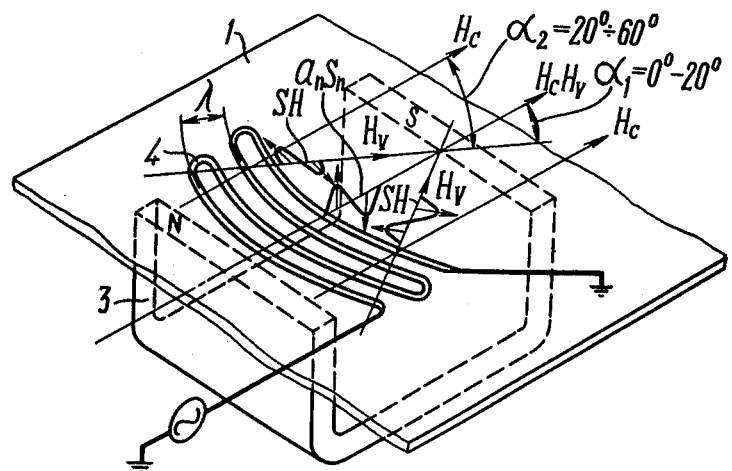
FIG. 10 shows a schematic of sounding a workpiece by a focused high-frequency transducer when two modes are excited in a uniform magnetizing field.
Figure 11:
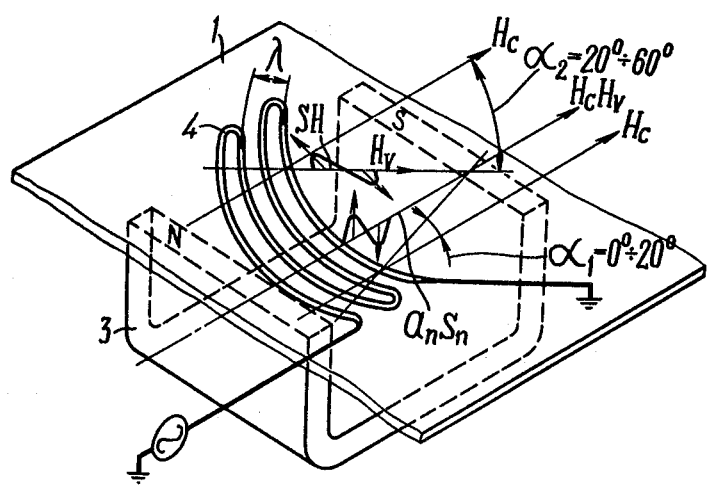
FIG. 11 shows a schematic of sounding a workpiece by a focused high-frequency transducer when two modes are excited in a uniform magnetizing field.

The proposed method for simultaneous excitation and reception of pulses of transverse and longitudinal waves focused in a specified point provides for significant increase in the sensitivity of testing. (FIGS. 10, 11). The method consists in acting on the surface of the test object 1 (FIGS. 10, 11) by a high-frequency electromagnetic field generated by a system of curved flat radiators 4 forming a comb-shaped structure and positioned discretely in the direction of radiation with a pitch divisible by a wave length λ. A magnetizing field is introduced into the test object 1 in the area of the high-frequency electromagnetic field by means of either a permanent magnet or an electromagnet, whose vector Hc is parallel to the surface of the test object 1. The interaction of the high-frequency electromagnetic field with the magnetizing field causes elastic displacements in the ferromagnetic workpiece 1. In case when the angles between the vector Hc of the magnetizing field and the direction of radiation of separate segments of the system of curved radiators 2 lie within the range of the angle $\alpha_1$ equal to ±(0° to 60°), transverse (SH) and longitudinal ($A_n$, $S_n$) plate waves are simultaneously excited in the workpiece (the mechanism of excitation being similar to the above described one). The segments of the system of curved radiators, to which the angle $\alpha_1$ amounts to ~0° - 20°, ensure excitation of mainly longitudinal ($A_n$, $S_n$) plate waves, whereas with $\alpha \approx \pm(20$ to $60)$ transverse (SH) plate waves are excited.

Figure 12:
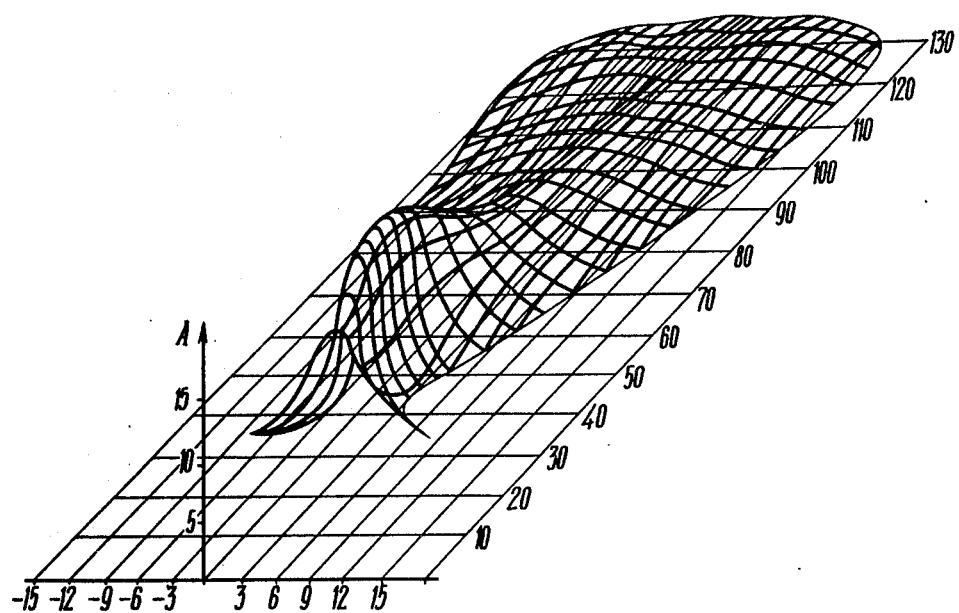
FIG. 12 shows the dependence of the amplitude of a plate wave pulse, which is the echo of the signal reflected from a drill-type flaw, on the position of the focused transducer with respect to the flaw.

Taking into consideration that radiation is directed normally to each segment of the radiator system, ultrasonic vibrations are focused in the direction of diminishing radius of radiators and diverge in the opposite direction. FIG. 12 illustrates the phenomenon of focusing ultrasonic vibrations. It shows a spacial amplitude characteristic of the ultrasonic field reflected from a cylindrical reflector with a 1 mm diameter. The illustration is presented in a three-dimensional rectangular coordinate system, which beginning coincides with the position of the reflector. Two coordinates on the plane (sheet) define the position of the center of the transducer, the rated value of the amplitude of the echo signal received by this transducer is plotted along the third coordinate axis. The transducer is made as a part of a flat circle limited by arcs with a radius of 38 to 52 mm and beams at an angle of 40°, wherein a system of flat radiators with a pitch of 2 mm is placed. The direction of the magnetizing field coincides with the axis of symmetry of the transducer. When the center of the transducer is positioned at a distance of 45 mm, which is equal to the focal distance, a distinct maximum of the reflected signal amplitude can be observed. Focused transducers are preferably employed for testing welded seams, when the distance to possible flaws is known. Electromagnetic acoustic (contactless) excitation and reception of ultrasonic plate waves permits testing workpieces in high vacuum conditions in the process of diffusion vacuum welding and in space conditions.

The longitudinal and transverse plate waves excited by the above described methods propagate in two opposite directions, each on its frequency and at its own group velocity. In this case, when the electromagnetic field is excited alternately at different frequencies, the system of flat radiators 2,4 (FIGS. 7, 10, 11) also alternately radiates this or that wave. When the electromagnetic field is excited by a wide frequency spectrum, two types of waves are radiated simultaneously. In case the group velocities of pulses of these waves are close, the wave pulses interact while propagating and this may result in distortion of test results. That is why reliable results can be obtained only when the minimum test base is found from the following expression:

$$L \geq \frac{\tau}{2} \cdot \frac{C_{y\,max} \cdot C_{y\,min}}{C_{y\,max} - C_{y\,min}}$$

where $\tau$ is the duration of the received pulse of plate waves, $C_{y\,max}$, $C_{y\,min}$ are group velocities of plate waves.

Figure 13:
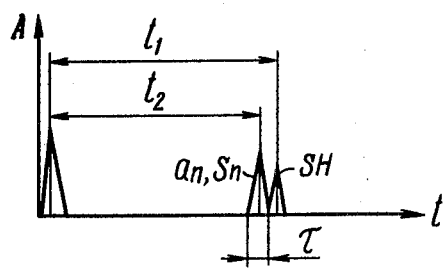
FIG. 13 explains determination of the minimum test base, that is the minimum distance at which reflected signals of two simultaneously excited modes can be observed separately.

This expression is easy to obtain, assuming that pulses of modes of transverse and longitudinal waves propagating at the group velocities $C_{y\,max}$, $C_{y\,min}$ cover the same distance 2L (for echo method) during the time $t_1$ and $t_2$, respectively (FIG. 13).

In this case the difference in time of pulse propagation on the test base L should be not less than $\tau$, that is $$\tau \leq t_1 - t_2$$

substituting $t_1 = (2/C_{y\,min})$ and $t_2 = (2/C_{y\,max})$ we receive $$\tau \leq \frac{2L(C_{y\,max} - C_{y\,min})}{C_{y\,max} \cdot C_{y\,min}}$$

wherefrom the expression for finding the minimum test base can be obtained.

As the diagrams of FIG. 9 indicate, the angle characteristic curves for longitudinal and transverse plate waves superimpose in a large range of angles and, though the intensity of signals differ significantly (tenfold), the method of alternate excitation of different types of waves should be preferred in this case. This also excludes false signals and increases reliability of test results.

By selecting modes of plate waves and work points on dispersion curves so that different types of flaws can be detected, it is possible not only detect such flaws reliably, but decipher their nature by separating in time excitation of various modes of plate waves.

Thus, for example, if for test of a 0.5 mm thick sheet $S_o$ mode of the longitudinal plate wave is chosen and the work point on the dispersion curve (FIG. 8) has $f \cdot d = 1$MCmm, where $f$ is the vibration frequency and $d$ is the sheet thickness, then the operational frequency should be $F = fd/d = 2$MC mm, the phase velocity of the mode $S_o$ with $fd = 1$MCmm $C_x = 5,000$ m/sec and the pitch of the flat radiators system should be $\lambda = C_x/F = 5,000$ m/sec/2MC = 2.5 mm. To excite a transverse plate wave by means of the same system of flat radiators, the zero symmetrical mode of the transverse wave SS(0) is selected, which has no dispersion and $C_x = C_y = 3,100$ m/sec. As the pitch of the flat radiators system is already set, the frequency for excitation of the SS(0) mode is determined according to the formula $f = C_x/\lambda = (3,100$ m/sec/2.5 mm) $= 1.24$ MC The group velocity of the $S_o$ mode in the selected work point $C_y = 5,200$ m/sec. With the pulse duration of 3 microsec. the minimum test base, that is the distance at which pulses of two modes $S_o$ and SS(0) reflected from a flaw can be separated amounts to $$L \geq \frac{3 \cdot 10^{-6} \text{sec}}{2} \cdot \frac{\frac{5,200 \text{ m}}{\text{sec}} \cdot \frac{3,100 \text{ m}}{\text{sec}}}{\frac{5,200 \text{ m}}{\text{sec}} - \frac{3,100 \text{ m}}{\text{sec}}} \approx 11.8 \text{ mm}$$

The minimum test base, that is the non-tested part of the workpiece, in this case is small. This can be attributed to the fact that group velocities of the selected modes of plate waves differ considerably. The optimal angle between the vector of the magnetizing field and the direction of propagation is selected by the curves of FIG. 9 and improved by experiment. For flaw detection work points are preferably selected on gentle slopes of dispersion curves (e.g. for $S_o$ mode it is advisable to work with $fd<1MC$ mm, for $A_o$ mode with $fd<2MCmm$) to reduce distortion of the pulse due to dispersion. With electromagnetic acoustical method of excitation of plate waves, longitudinal symmetrical waves in particular, work point are preferably selected on horizontal portions of dispersion curves (e.g. for $S_1$ mode it is admisable to work with $fd = 4MCmm$), where the phase velocity of plate waves is equal to the velocity of longitudinal waves and the plate wave contains only the tangential shifting component which is uniform throughout the thickness of the workpiece (plate), which ensures uniform detection of flaws throughout the thickness of the workpiece.

If both modes selected for testing possess dispersion, the operational frequencies are easier determined by experimentally adjusting the generator frequency until the maximum signal of the selected mode is obtained. For example, the system of flat radiators with a pitch $\lambda = 2.8$ mm can be used to excite in a 1 mm thick steel sheet $A_1$ mode at the frequency 2.4 MC, mode $S_o$ at the frequency 1.7 MC, mode $A_o$ at the frequency 0.75 MC, mode SS(1) at the frequency 1.9 MC, mode SS(0) at the frequency 1.1 MC.

Figure 14:
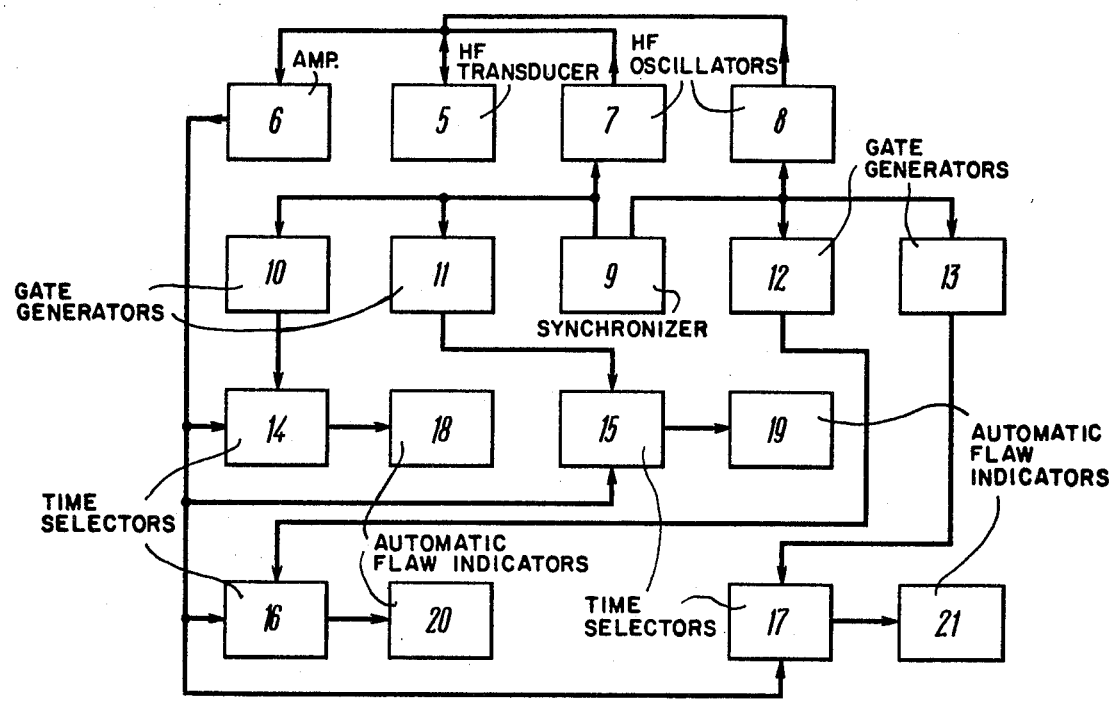
FIG. 14 shows a functional diagram of a device realizing separate detection of a flaw by two different modes.
Figure 15:
FIGS. 15 - 28 show time separation of echo signals of two different modes.
Figure 16:
Figure 17:
Figure 18:
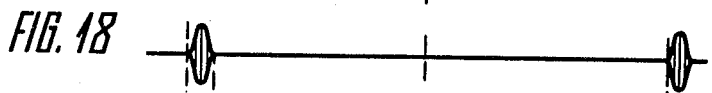
Figure 19:
Figure 20:
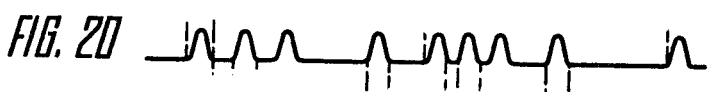
Figure 21:
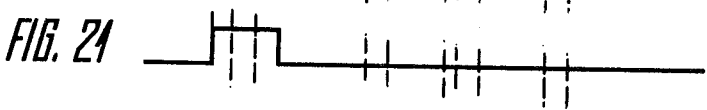
Figure 22:
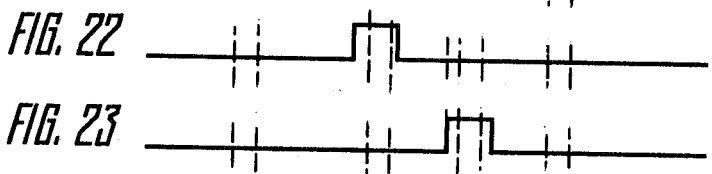
Figure 23:
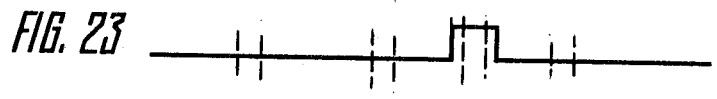
Figure 24:
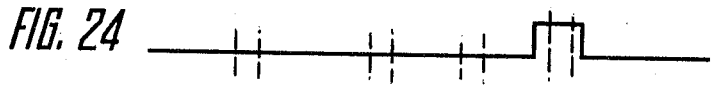
Figure 25:
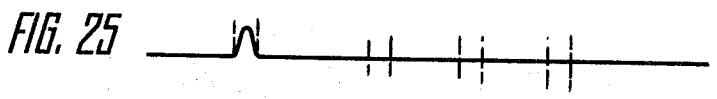
Figure 26:
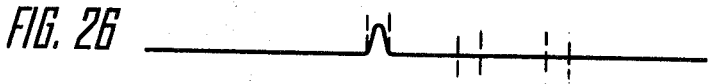
Figure 27:
Figure 28:

FIG. 14 shows an example of a functional diagram of a device for testing by two different modes with separate signalling about a flaw detected by the use of each mode.

The device of FIG. 14 comprises a high-frequency transducer 5 connected to a wide-band amplifier 6 and high-frequency oscillators 7 and 8 coupled to a synchronizer 9. The synchronizer 9 is connected to the inputs of gate generators 10, 11, 12, 13 which outputs are connected to the inputs of time selectors 14, 15, 16, 17 which second inputs are connected to the wide-band amplifier 6 and the outputs are joined to automatic flaw indicators 18, 19, 20, 21.

The high-frequency transducer 5 is positioned in the middle of the test object (band) so that the direction of radiation is perpendicular to the edges of the workpiece (band). In this case the electromagnet of the magnetizing device is positioned so that the direction of the vector of the magnetizing field is at approximately 20° to the direction of propagation of a plate wave. The operation of the electronic pack of the device is explained by the diagrams of pulses of FIGS. 15 to 28.

The synchronizer 9 works out pulses (FIGS. 15, 16, 17) one of which (the pulse of FIG. 16) starts the high-frequency oscillator 7 which generates a pulse (FIG. 18) operating on the frequency ensuring excitation in the workpiece of a longitudinal normal wave, e.g. of the $S_o$ mode. Another pulse (FIG. 17) starts the generator 8 which produces a pulse (FIG. 19) operating on the frequency ensuring excitation in the test object of a transverse plate wave, e.g. of the SS(0) mode devoid of dispersion and detecting flaws irrespective of their position within the workpiece. The pulse (FIG. 16) of the synchronizer 9 (FIG. 14) starts the gate generator 10 which forms a pulse (FIG. 21), which leading edge coincides with the end of the emission pulse of the generator 7 (FIG. 14) and the trailing edge coincides with the leading edge of the pulse reflected from the edge of the workpiece, the gate generator 11 which forms a gate pulse (FIG. 22) which time position corresponds to the pulse of the longitudinal plate wave twice reflected from the edges. The pulse (FIG. 17) of the synchronizer 9 (FIG. 14) starts the gate generator 12 which forms a pulse (FIG. 23) which leading edge coincides with the end of the emission pulse of the generator 8 (FIG. 14) and the trailing edge coincides with the leading edge of the pulse reflected from the edges of the workpiece. The gate generator 13 forms a pulse (FIG. 24) which time position corresponds to the twice reflected from the workpiece edges signal of the transverse plate wave. The pulses received by the transducer 5 (FIG. 14) are fed to the input of the wide-band amplifier 6 and from its output the pulses (FIG. 20) are fed to the inputs of the time selectors 14, 15, 16, 17 (FIG. 14). The second input of the selector 14 receives the gate pulse from the generator 10. The pulse (FIG. 25) corresponding to the flaw is supplied from the output of the selector 14 to the automatic flaw indicator, which gives a signal about the flaw detected by the mode $S_o$. The second input of the selector 15 (FIG. 14) receives a gate pulse from the generator 11. The pulse (FIG. 26) corresponding to the signal of the longitudinal plate wave twice reflected from the edges is supplied from the output of the selector 15 to the automatic flaw indicator 19 (FIG. 14), which, when the pulse reduces or disappears, gives a signal about a major flaw or instrument failure. The input of the selector 16 receives a gate pulse from the generator 12. The pulse (FIG. 27) corresponding to the flaw is supplied from the output of the selector 16 to the input of the automatic flaw indicator 20 (FIG. 14), which generates signals about the flaw, like pores, non-metallic inclusions, etc., detected by the mode SS(0). The second input of the selector 17 receives a pulse from the generator 13. The pulse (FIG.28) corresponding to the signal of the transverse plate wave reflected twice from the edges is supplied from the output of the selector 17 to the automatic flaw indicator 21 which, when the pulse reduces or disappears, generates signals about a major flaw or instrument failure.

When the test base is sufficient for time separation of signals of two modes, it is possible to employ one generator, a wobbler, but the gate of the test zone in this case contains pulses of both the longitudinal and transverse plate waves reflected from a flaw and the mode of the reflected pulse cannot be determined.

Figure 29:
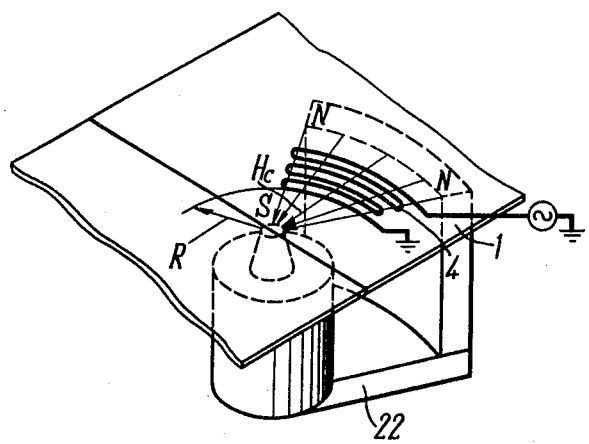
FIG. 29 shows a schematic of sounding of a transverse welded seam of workpiece (strip) by a focused transducer with a focused magnetizing field.

In testing workpieces like welded pipes or sheets, when similar flaws can occur in a previously known zone, e.g. in a welded seam, it is advisable that only longitudinal plate waves be used focused in the zone of the welded seam of the workpiece. The method of excitation of a longitudinal plate wave (Lamb wave) focused in a specified point (FIG. 29) consists in that the surface of the workpiece 1 is acted upon by a high-frequency electromagnetic field excited by a system of curved flat radiators 4 and the vector of the magnetizing field induced in the workpiece 1 by a permanent magnet or an electromagnet 22 is directed in accordance with the radiation direction. In this case the radius of separate curved flat radiators 4 is selected equal to the distance to the focusing point which is located directly on the welded seam and their length is equal to the effective width of the magnetizing field. In this case the process of testing is effected by moving the device along the seam.

There can be an embodiment of the device for realization of the method, wherein both poles of the magnet are parts of rings with a respective radius of curvature.

With the through transmission method of flaw detection, when it is required to separate the output of the generator and the input of the amplifier to eliminate overloading the amplifier by the powerful ultrasonic generator pulse, excitation and reception of ultrasonic vibrations are done by different transducers. In pulsed excitation of plate waves a spectrum of vibrations of different frequencies propagates in the workpiece, which depends on the shape of the pulse. Since the phase and group velocities of plate waves depend on the frequency, the pulse is subjected to dispersion distortions resulting in changes of its amplitude, duration and frequency, that is the wavelength, which depend on the shape of the pulse, on the position of the work point on the dispersion curve and on the distance covered by the pulse.

With separate excitation and reception of plate waves, it is advisable that dispersion distortions of the pulse, which has passed the test base, are taken into consideration. Theoretical calculation of dispersion distortions is complicated. The work by L. V. Verevkina and L. G. Merkulov "Calculation of Dispersion Distortions of Normal Waves Pulses", USSR Academy of Sciences, "Fault Detection" magazine, No. 5 1969, Nauka Publishers, supplies a method of an approximate calculation of dispersion distortions of pulses with a Gauss envelope (bell-shaped), which is also too complicated and brings in errors, when used for practical purposes.

It is therefore advisable in estimating the influence of dispersion on the pulse parameters to make use of the experimental results. Experimental measurement of an average wavelength in the plate wave pulse which has covered a specified distance presents no difficulties. Measurements are done by superimposition method and can be fulfilled either by one system of flat radiators, which operates in a combined regime, or by three systems of flat radiators, one for transmission and two for reception.

Figure 30:
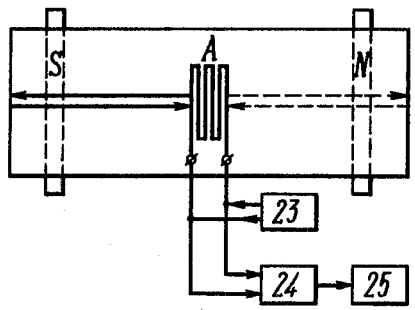
FIG. 30 shows a functional diagram of measuring a wave length by one transducer.
Figure 32:
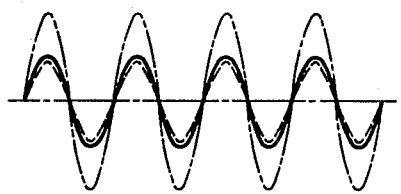
FIGS. 32, 33 explain addition of pulses when measuring a wave length, in phase and antiphase, respectively.
Figure 33:
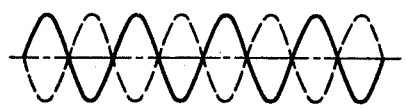

The diagram for measuring a wavelength by means of one system of flat radiators operating as a transmitter-receiver system is shown in FIG. 30. The system of flat radiators A is positioned in the middle of the workpiece and connected to the output of a generator 23 and the input of an amplifier 24 which output is connected to an indicator 25. The direction of ultrasonic vibrations radiation is perpendicular to the edges of the workpiece. The frequency of the generator 23 is adjusted to obtain optimal excitation of the mode, the mean period of pulse filling ($T_{mean}$) being measured by an oscillograph. The signals reflected from the edges of the workpiece are summed up and, when radiators are moved by the measuring screw, the indicator 25 displays maximums (FIG. 32) when signal come in phase and minimums (FIG. 33) when the radiators are displaced by $\lambda/4$ and signals come in antiphase (shifted to $\lambda/2$). Displacement of radiators is measured by the micrometer to find out when "$n$" minimum of the signal is observed, that is the displacement $S = n\lambda/4$.

Figure 31:
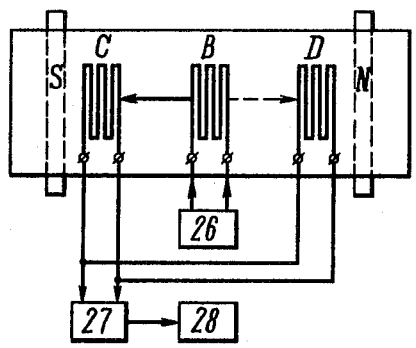
FIG. 31 shows a functional diagram of measuring a wave length by three transducers.

The diagram for measuring a wavelength by means of three systems of flat radiators is shown in FIG. 31.

The system of flat radiators B, C and D are arranged on one axis. The transmitting flat radiator system B is placed in the middle and connected to the output of the generator 26. Two receiving flat radiator systems C and D are coupled to the input of an amplifier 27. The summary signal is supplied from the amplifier 27 to an indicator 28. The transmitting system can be moved by a micrometer screw and the micrometer measures the displacement at which "$n$" minimums are observed in this displacement $S = n \cdot \lambda/2$.

After measurements of the wavelength and the pulse filling frequency $f = 1/T_{mean}$, the phase velocity is calculated $C_x = f$. The group velocity is calculated according to the formula $C_y = L/t$, where L is the distance covered by the pulse during the time $t$. Measurements have indicated that the wavelength precisely coincides with the pitch of the flat radiator system only for the mode SS(0) which has no dispersion. With modes possessing some dispersion the wavelength differs from the pitch of the flat transmitting radiator system.

It is therefore proposed to determine, according to the invention, the pitch of the receiving system for a specified base proceeding from the results of measurements of the average wavelength in a pulse. This increases the accuracy of equipment adjustment, reliability of its operation and test results.

The above discussed method for measuring the wavelength, which permits determination of the phase velocity of the received plate wave, combined with the method for measuring the group velocity ensures defining the type of a wave in those instances when it cannot be determined in advance.

When working with test objects with a rough surface, the high-frequency transducer is quickly worn out and the insulation of the high-frequency transducer can be broken down to the test object. For testing thin workpieces the weight of an electromagnetic acoustic transducer is to be preferably reduced. Therefore, the magnetizing device and the high-frequency transducer are preferably made separate and the high-frequency transducer is provided with an electrically strong and mechanically durable protector.

Figure 34:
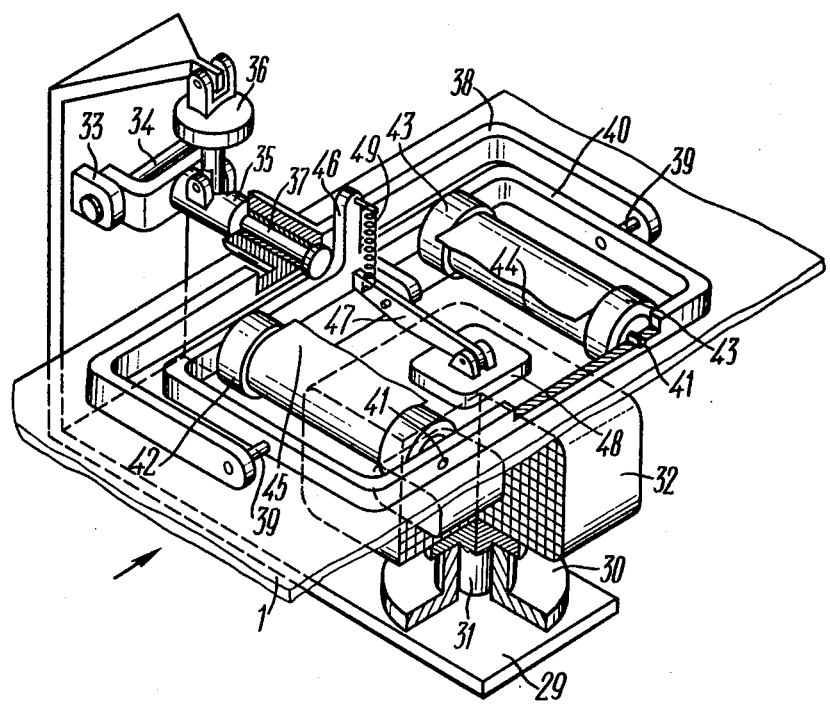
FIG. 34 shows mutual arrangement of the test object, the system of flat radiators with a leverage and the magnetizing device.

A device (FIG. 34) for realization of the method for excitation and detection of ultrasonic plate waves comprises a foundation 29 which carries a magnetizing device mounted in a bushing 30 on a vertical axle 31 and made as a solenoid 32 which can be rotated in the horizontal plane and later locked in a specified position.

A leverage 35 equipped with a lifting drive 36 is mounted on a bracket 33 on an axle 34. A fork 38 is secured to the leverage 35 by means of a joint 37 and a bearer frame 40 is fitted by semiaxles 39 thereon. A protective gear made as two rollers, which are corbelled cylindrical members, mounted on parallel axles 41 in the frame 40 in one plane. The sides 43 of the rollers 42, which are in contact with the surface of the test object 1, have the maximum diameter and covered by a layer of material ensuring good coupling with the surface of the workpiece 1. A middle portion 44 of the rollers 42 with a somewhat smaller diameter carries an elastic, electrically strong and mechanically durable ring band 45, the middle portions 44 of the rollers 42 acting as pulleys.

A high-frequency transducer 48 is mounted on a bracket 46 of the frame 40 by means of a leverage 47. The transducer 48 is encased in a protective cover and pressed against the surface of the test object 1 by a spring 49.

The device operates as follows. When the test object 1 approaches the zone of the device, the drive 36 is switched on, the leverage 35 is lowered pressing the rollers 42 to the surface of the test object 1. The cylindrical portions of the rollers 42 covered by a coupling material start rotating when in contact with the test object 1. If in the process of testing the rollers 42 rotate without slips as the test object 1 moves along, the linear speed on the surface of the roller 42 is equal to the speed of travel of the test object 1. The linear speed of the ring band 45 fitted on the smaller diameter portions 44 of the rollers 42 can be practically taken equal to the linear speed on the surface 43 of the roller, which is in contact with the test object 1. In this way the speed of the protective band 45 moving under the high-frequency transducer 48 coincides in magnitude and direction with the travelling speed of the test object 1. Taking into account the fact that the band 45 is practically immovable with respect to the test object 1, the wear of the band 45 is insignificant, even if the surface of the test object 1 is rough. At the same time, the high-frequency transducer 48 travels along the band 45, which surface has but a small frition coefficient, and the wear-out of the high-frequency transducer 48 is also minimum. The leverage 35, the joint 37, the fork 38, the frame 40 mounted on the semiaxles 39 permit in the process of testing the rollers 42 to follow the surface of the test object 1 when its position with respect to the device changes. The leverage 47 equipped with the spring 49 ensure that in the process of testing the high-frequency transducer 48 follows the surface of the test object 1.

In the process of adjustment, when the solenoid 32 is turned about the axle 31 in the bushing 30, the angle is changed between the vector of the magnetizing field produced by the solenoid and the direction of radiation, thus ensuring excitation of this or that type of plate waves. In case two types of waves are to be used simultaneously, the described device should be employed together with the electronic device of FIG. 14 which has been earlier described. The device of FIG. 34 permits effective excitation and detection of plate waves with considerable changes in the position of the workpiece with respect to the magnetizing device, because the proposed construction reduces the effect of variations of the clearance between the test object and the magnetizing device. This is illustrated by the diagram of FIG. 35 supplying the dependence of the signal amplitude on the distance of the tested sheet to the magnet poles ("m" curve) and to the surface of the solenoid ("n" curve).

The diagram indicate that the dependence of the signal amplitude upon the distance from the tested object to the solenoid ("n" curve) is more smooth in the 40 to 50 mm range. This ensures less effect of the workpiece play on the signal, when it travels in the process of testing at a high speed with respect to the solenoid.

The fact that the magnetizing device and the high-frequency transducer are made separate permits, apart from what has been said above, reduction in weight and increase of accuracy in following the surface of the workpiece by the transducer.

Employment of the proposed device ensures realization of the discussed methods for excitation and reception of ultrasonic plate waves for workpiece testing in conditions of metallurgical works at a test speed of 10 m/sec.

In continuous rolling of strip (sheet) steel the end of the preceding roll and the beginning of the next roll are butt welded to increase the speed of rolling. The reliability of the mill depends on the quality of the welded seam and testing the quality of the butt seam becomes vital in the production process. Testing is required for detection and cut-out of faulty seams to exclude rupture in further processing, e.g. in rolling mills, since they can cause considerable losses, involving damaged equipment, lost time of the mill and losses of rolled steel discharged as a result of the rupture. Seam testing should be done at a high speed to keep up with the plant and at high temperatures of the seam (up to 500° – 600° C). The seam can be tested after dressing, when the strip is immobile and the seam is in a fixed position, or during the strip movement. The strip travelling at a speed of up to 7 m/sec can be immersed in water and its surface can be covered by water or oil drops.

A similar task arises in welding steel strip rolls in the operation of pipe-welding machines. In this case the high quality of butt welds ensured by adequate welding conditions and guaranteed by ultrasonic testing permits employment of butt-welded pipes as a standard product.

FIG. 36 shows a device for testing a welded seam of a steel strip in the operation of continuous plants or pipe-welding machines.

A device (FIG. 36) for testing the quality of a butt welded seam of a strip 50 comprises two guides 51 positioned along the strip 50. One guide 51 carries a platform 52 with an electric drive 53 mounted in its middle part. An electromagnetic hold 54 is set on one edge coaxially with the guide 51. A bracket 55 secured on an axle 56 and a stop 57 are placed over the strip 50. A spring 58 is fitted external to the platform 52. A guide 60 with a carriage 61 is installed on the bracket 55 across the strip 50 along a welded seam 59 and a welded seam position sensor 62 is placed at the end of the bracket 55 over the edge of the strip 50 and connected to an electromagnetic hold 63. The free end of the guide 60 is provided with a supporting roller 64 resting on the other guide 51 and a lug 65, whereon a welded seam position sensor 66 is positioned and coupled to an electromagnetic hold 67. The carriage 61 mounts an electric drive 68, a bracket 69 installed on a leverage 70 equipped with a lifting drive 71 and contacting the strip 50 by means of a roller 72. A magnetizing device 73 mounted on the bracket 69 is secured on an axle 74. The axle 74 fits one of the pole shoes 75 positioned over the tested seam 59. A second pole shoe 76 is made with a crosssection shaped like a part of a ring. Such combination of pole shoes shapes permits induction of a magnetizing field diverging from the welded seam in the strip. A high-frequency transducer 79 is mounted by means of a leverage 78 on the magnetizing device 73 on an axle 77. In the initial position of the device the platform 52 is kept stationary with respect to the guide 51 by the magnetic hold 54. The carriage 61 is near the bracket 55. The bracket 69 of the carriage 61 is lifted over the strip 50 to be tested by means of the drive 71. The bracket 55 is kept by the spring 58 in a counterclockwise turned position with respect to the platform 52 and pressed against to the stop 57. The guide 60 is also turned and makes an acute angle with the welded seam of the strip 50. When the strip 50 starts travelling from left to right, the first to lock the welded seam 59 is the seam position sensor 66 actuating the electromagnetic hold 67. When the hold 67 works, the guide 60 turns together with the bracket 55 about the axle 56 on the platform 52 and the spring 58 is stretched. At the moment the welded seam 59 passes under the sensor 62, its command actuates the electromagnetic hold 63. Here, the guide 60 which is parallel to the line connecting the seam position sensors 62 and 66 becomes also fixed with respect to the strip 50 by the hold in a position parallel to the welded seam 59. When the second electromagnetic hold 63 operates, the electromagnetic hold 54 of the platform 52 is disconnected and the guide 60 moves with the strip 50. As the device and the strip 50 travel together, the drive 71 is switched on to lower the bracket 69, as well as the drive 68 of the carriage 61 which moves the high-frequency transducer 79 with the magnetizing device 73 along the welded seam 59 under test. The test being over, the electromagnetic holds 63, 67 are released, the drive 53 of the platform 52 is switched on to move the platform 52 in the direction opposite to the direction of the tested strip 50. The bracket 69 on the carriage 61 is lifted by the drive 71 and the electric drive 68 is reversed. The carriage 61 is brought back to the initial position. When the platform 52 reaches its initial position, it is locked by the electromagnetic hold 54. After this the device for testing the quality of the welded seam of the strip 50 is ready for testing the next seam.

For adjustment of the device the angle between the radiation direction and the seam, as well as the optimal for the selected modes angle between the direction of the vector of the magnetizing field and the radiation direction. The angle between the radiation direction and the seam is set by turning the magnetizing device 73 together with the leverage 78 and the transducer 79 about the axle 74 and then locking the device. The second adjustment is done by turning the axle 77 with the high-frequency tranducer 79 secured thereto by the leverage 78. This adjustment permits changing the angle between the direction of the vector of the magnetizing field and the direction of radiation for excitation of transverse normal waves in accordance with the above described method. The pole shoe 75 coinciding with the welded seam is replaceable. If a round pole shoe is used, a radially diverging from the pole shoe field becomes dominant. In combination with the focused high-frequency transducer it ensures excitation of normal waves focused in a specified point.

A pole shoe of rectangular cross-section should be used to widen the test zone. In this case a uniform magnetizing field of one direction is dominant in the workpiece plane. In combination with a transducer with rectilinear sections and the angle between the vector of the magnetizing field and the direction of radiation being other than zero, it ensures excitation of transverse plate waves of a more uniform intensity with the distance from the high-frequency transducer. This permits wider test zone and also testing the near-seam area of the metal. Adjustment of the angle between the vector of the magnetizing field and the direction of radiation in the test device is done by turning the axle 77 and subsequent fixing the position.

The device can be employed to test stationary workpiece seams. In this case its operation becomes much more simple.

The device can be equipped with a paint marker, recorder and coupled to a system for cutting out faulty welded seams.

Figure 37:
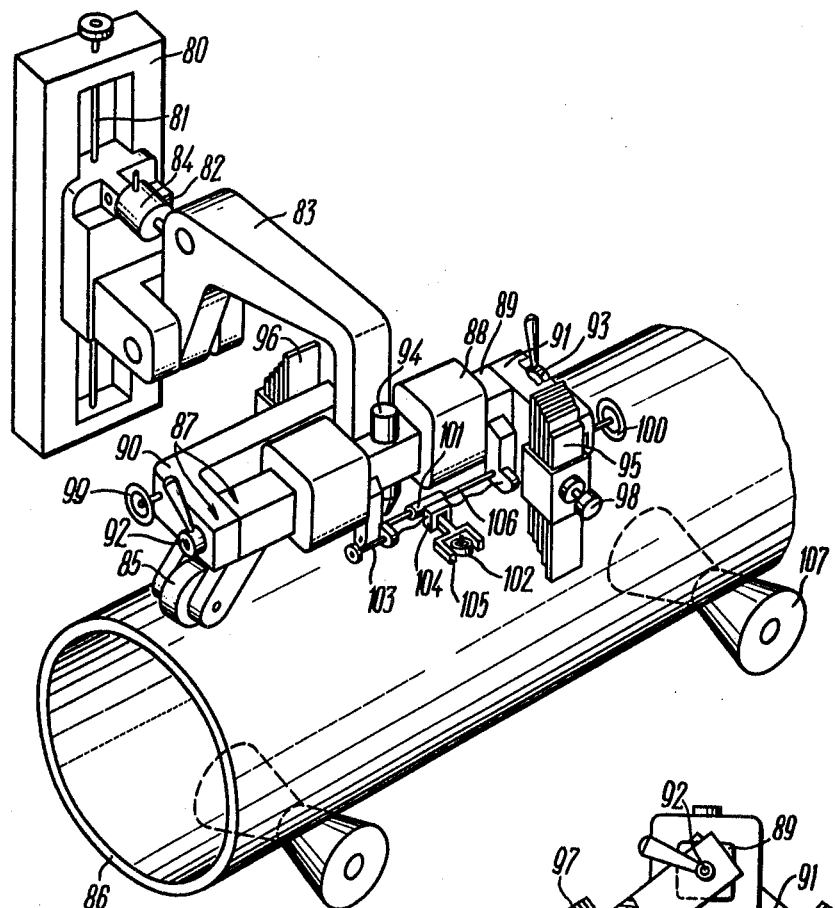
FIGS. 37, 38 show a pipe testing device.

One of the embodiments of devices for realization of the proposed methods for excitation and reception of plate waves is a device for testing the quality of seamless and electrically welded pipes with a diameter of 150 − 200 mm and more. This device (FIG. 37) for pipe testing comprises a supporting vertical guide 80 with a screw drive 81 intended for adjustment the height of the device, a floating bracket 82 which carries by means of a leverage 83 provided with a lifting drive 84 a magnetizing device 87 mounted on guiding rollers 85 contacting a test object (pipe) 86. This magnetizing device 87 is the basic unit for other construction elements to be secured thereto. The magnetizing device 87 comprises coils 88 which are in opposite connection a sectionalized S-shaped magnetic circuit 89 with a core 89 and levers 90 and 91, made adjustable by means of joints 92 and 93 and coinciding with the axis of the core 89.

Figure 38:
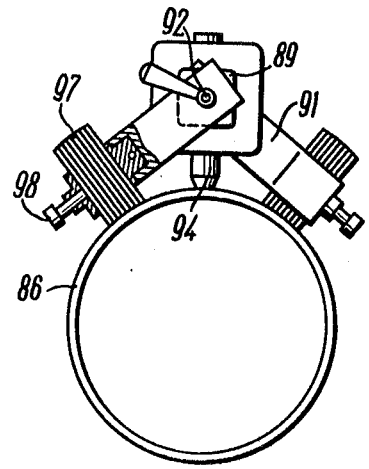
Figure 39:
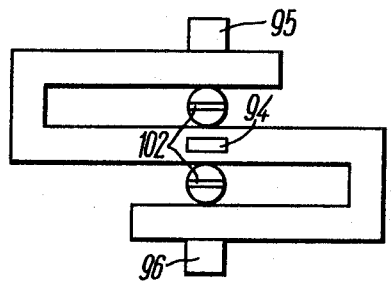
FIGS. 39 - 42 show pipe sounding schematics.
Figure 40:
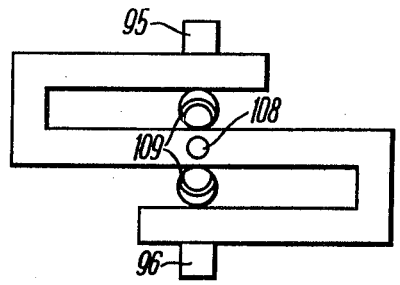
Figure 41:
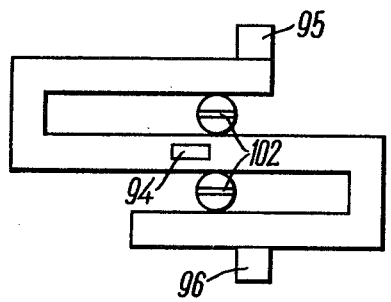
Figure 42:
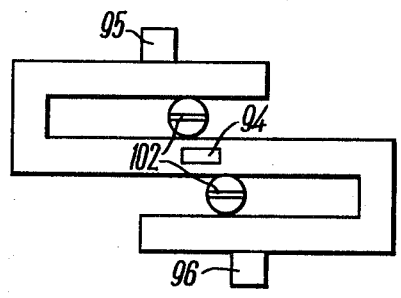

To adjust the direction of the magnetization field in the body of the pipe 86 the S-shaped magnetic circuit is provided with three pole shoes which are in direct contact with the pipe under test. The central pole shoe 94 is interchangeable and can be round or rectangular in the cross-section contacting the pipe 86. Two other pole shoes 95 and 96 positioned at the ends of the S-shaped magnetic circuit can be adjusted along the pipe and are assembled of plates 97 (FIG. 38) secured in an adjusting and fixing unit which is a housing with fixing members 98. When adjusting to a specific tested diameter of the pipes 86, the packs of the plates 97 of the pole shoes 95, 96 are deformed so that the butts of the plates 97 follow the shape of the pipe 86 at the place of contact. The pole shoes 95, 96 are shifted in the process of adjustment by means of screw pairs 99, 100. High-frequency transducers 102 adjustable along the pipe 86 are mounted on the core 89 of the magnetizing device 87 symmetrically to the axis of the pipe 86 by means of leverages 101. Adjustment of the position of the transducers 102 along the pipe 86 is done by screw pairs 103 joined to nuts 104. The cross slots of the nuts 104 allow travel of a fork 105 with the transducer 102 and turning of the forks 105 on an axle 106 during testing so that the high-frequency transducer follows the surface of the pipe 86. The high-frequency transducers 102 can rotate about an axis coinciding with the normal to the pipe surface to ensure changes of the angle between the radiation direction and the magnetizing field.

The device operates as follows. When the pipe 86 under test travels along rollers 107 into the test zone, the magnetizing device with the high-frequency transducers 102 is lowered by the drive 84 until the rollers 85 touch the pipe 86. A permanent magnetizing field is induced in the pipe body through the pole shoes 94, 95, 96. This field constitutes a certain angle with the direction of radiation of the high--frequency transducer, which depends upon the mutual position of high-frequency transducers and the pole shoes 94, 95, 96.

Similarly to the earlier described methods for excitation and reception of plate waves the device (FIG. 37) ensures excitation and reception of this or that type of plate waves.

Depending on the mutual position of the high-frequency transducers 102, either the shadow method of detecting flaws, which are oriented differently in the pipe cross-sections, can be realized or the echo method of testing by sounding the pipe body in different directions by each transducer. When focused high-frequency transducers are employed, the same methods can be realized with localization of the test zone. This embodiment can be used for testing the pipe welded seam.

By changing the mutual position of the pole shoes 95, 96 and the high-frequency transducers the angles can be changed between the direction of the magnetizing field and the direction of radiation of the high-frequency transducers. Such angles can be selected which provide for exciting different types of waves: plate longitudinal, transverse waves or both types of waves in accordance with the above described methods.

When operating the device various testing procedures can be realized. Some of them are shown in FIGS. 39 – 42. When a wide zone is tested by the through transmission method (FIG. 39) the high-frequency transducers 102 with rectilinear sections are placed opposite each other, the rectangular central pole shoe 94 is selected and the adjustable pole shoes 95, 96 are brought on a line with the high-frequency transducers 102. In this case the plate wave pulse excited by one of the transducers 102 propagates in the pipe wall and is attenuated, if there is a flaw, and detected by the other transducer with a lesser amplitude.

When through transmission testing by longitudinal plate waves a localized pipe zone (FIG. 40), the arrangement of the pole shoes 95, 96 and transducers 109 remains the same but the central pole shoe 94 is of a round cross-section and the high-frequency transducers 109 are focused. In this case sensitivity to flaws positioned in the focus is increased. The sounding zone during testing according to diagrams of FIGS. 39, 40 can be selected either in the clearance between the transducers or external thereto. Test diagrams of FIGS. 39 and 40 allow testing by one of the two transducers by the echo pulse method by longitudinal waves ($A_n$, $S_n$) and by the other transducer by transverse plate waves (SH). For this purpose the pole shoe 95 is to be shifted to the left so (FIG. 39) that the angles between the normal to the sections of the winding of the transducer 102 and the line connecting the pole shoes 94 and 95 are within the range $\alpha$ equal to 10° to 60°.

With the shadow pipe testing method by plate waves (FIG. 41) the high-frequency transducers 102 and the pole shoes 94, 95, 96 are positioned so that the directions of the magnetizing fields and the directions of radiation make an angle within 10° to 60°.

With the echo pipe testing method by transverse or simultaneously by transverse and longitudinal plate waves (FIG. 42) the pole shoes 95, 96 (the central shoe being rectangular in cross-section) are placed at an angle to the pipe axis. The transducers 102 with rectilinear sections are arranged so that the direction of the magnetizing field and the direction of radiation are at an angle lying within the 10° to 60° range. The transducers radiate either a transverse (SH) plate wave or simultaneously transverse (SH) and longitudinal ($A_n$, $S_n$) waves across the pipe 86.

The pulses reflected from flaws are detected by the transducers which generated these pulses. The received signals can be amplified, deciphered and recorded by means of electronic equipment similar to that described above (FIG. 14). Test results recorders and processing equipment can also be used.

The above described embodiments do not exhaust all possible variations of mutual arrangements of transducers and pole shoes and respective test methods which can be realized. The high-frequency transducers 102 and 109 which housing is made of plastic materials with a low melting point are to be employed in the above described embodiments. The assembled transducers (with windings) are deformed when heated on the surface coinciding with the surface of the pipe being tested. To ensure adequate wear resistance the transducers are provided with durable insertion members contacting the pipe surface.

Figure 43:
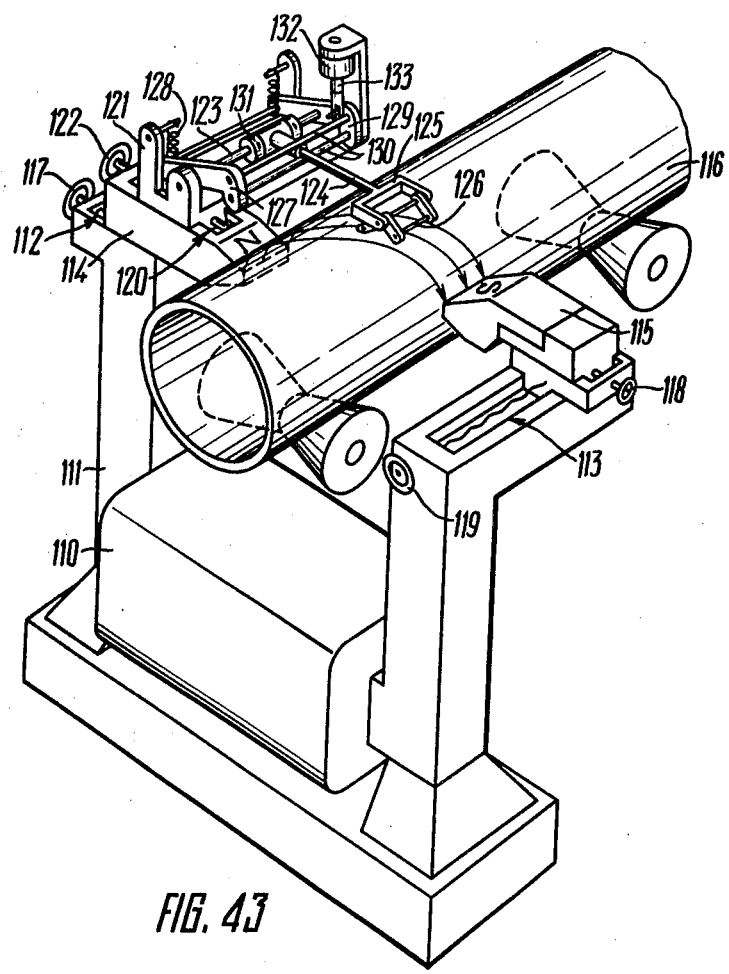
FIG. 43 show a device for testing pipes of small diameter.

The device of FIG. 43 can be more effectively employed for testing pipes of small diameter (20 to 100 mm). The device comprises a magnetizing device featuring a coil 110 and a U-shaped magnetic circuit 111 which end portions are made as guides 112 and 113. Pole shoes 114 and 115 mounted on the guides 112 and 113 can be moved, the pole shoe 114 being adjustable in the transverse direction with respect to a pipe 116, whereas the pole shoe 115, besides being interchangeable, can be adjusted along the pipe 116. The pole shoe 114 is moved by a screw drive 117, whereas the pole shoe 115 can be moved across and along the pipe by means of respective screw drives 118 and 119.

The pole shoe 114 made as a guide 120 carries a bracket 121 which can be shifted in the process of adjustment by a screw drive 122 in the direction across the tested pipe 116. The bracket 121 carries a cylindrical guide 123 mounting a leverage 124 equipped with a fork 125 with a transducer 126 hinged thereto. The high-frequency transducer 126 is pressed against the surface of the test pipe 116 by means of a leverage 127 mounted on the cylindrical guide 123 and held against the surface of the pipe 116 by cylindrical springs 128. A second end 129 of the lever of the leverage 127 is made as two tie rods 130 between which the arm of the leverage 124 is fitted, said leverage 124 carrying the high-frequency transducer 126 in the fork 125. Such design allows to move the high-frequency transducer along the pipe 116 during adjustment maintaining the force pressing it against the pipe constant. The high-frequency transducer 126 is fixed in the longitudinal direction with respect to the pipe 116 after the adjustment by locking rings 131. The leverage 124 with the transducer 126 is lifted and lowered by a lifting drive 132 mounted on the bracket 121 and connected to the lever 129 by a rod 133.

The device permits mounting a second high-frequency transducer (not shown in FIG. 43) placed symmetrically to the shown transducer 126.

Before the pipe 116 approaches, the transducer 126 is raised over the pipe. When the pipe end enters the test zone, the high-frequency transducer 126 is pressed against the surface of the pipe 116 by the lifting drive 132. The device should be adjusted each time the diameter of the pipe to be tested changes. When pipes of a definite diameter are tested, the device is adjusted to excite one type of waves by changing the mutual arrangement of the high-frequency transducer 126 and the pole shoes 114, 115 by means of the drive 119 and shifting the high-frequency transducer 126 along the guide 123. When longitudinal normal waves are to be used for testing, the pole shoes 114, 115 and the high-frequency transducer 126 should be aligned on one line across the pipe 116 direction. When adjusting the device for operation with transverse plate waves, the pole shoe 115 is shifted by the drive 119 and the high-frequency transducer 126 is shifted along the guide 123 with respect to the pole shoe 114 along the pipe 116 so that the angle between the direction of the magnetizing field and the direction of radiation is selected within the 10° to 60° range in accordance with the above described method for excitation and detection of plate waves. When the diameter of tested pipes 116 changes, the pole shoes 114, 115 are separated by the drives 117, 118 respectively and the high-frequency transducer 126 is brought by the drive 122 across the axis of the pipe 116 to the vertical plane coinciding with the axis of the pipe 116. This adjustment is followed by the operations of the first stage.

It should be noted that the transducer 126 used in this device is preferably made on a comb-shaped frame from elastic material, the sections of the high-frequency winding being placed in its grooves. Such design of the transducer permits the frame to be deformed and assume the shape of the test pipe surface, maintaining permanent clearance between the winding sections and the pipe surface.

In testing workpieces by plate waves, the mode of the normal wave and the position of the work point on the dispersion curve should be correctly selected. That is why in testing workpieces of different thicknesses a large set of high-frequency transducers with different pitch is required. To increase the adjustment speed, when testing workpieces of different thicknesses, a high-frequency transducer with a variable pitch is preferably employed.

Figure 44:
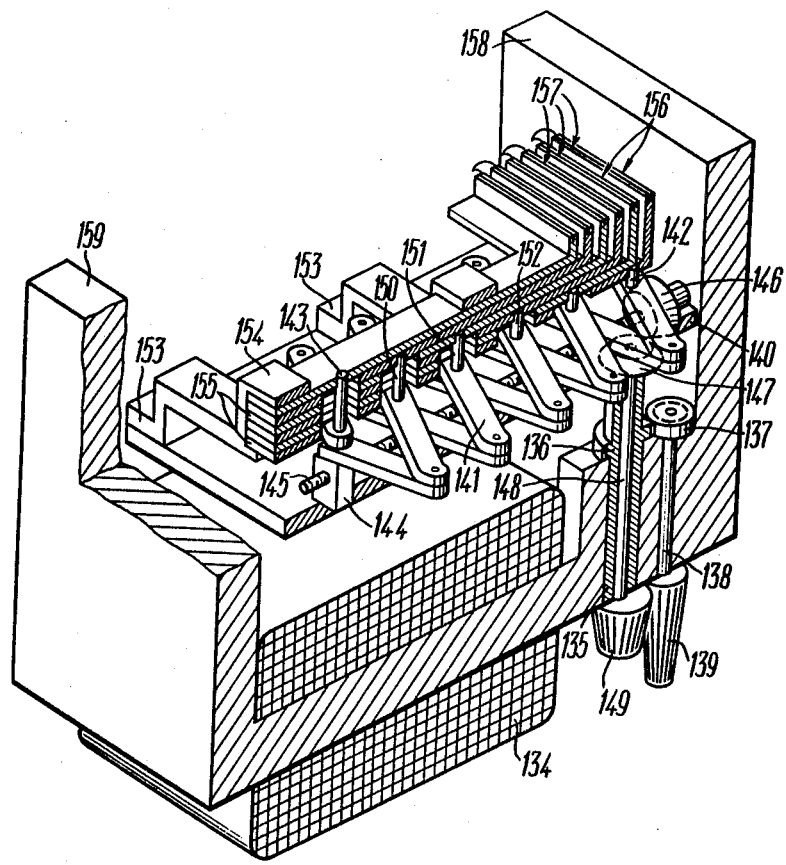
FIG. 44 shows a device for testing sheets by plate waves by means of a high-frequency transducer with an adjustable pitch.

A device (FIG. 44) for testing sheet material by means of longitudinal and transverse plate waves comprises a magnetizing device, a turning mechanism secured thereto for selection of the angle between the magnetizing field and the direction of radiation of a high-frequency transducer with an adjustable pitch. The magnetizing device comprises a U-shaped magnetic circuit with a coil 134. The turning mechanism comprises a bushing 135 fit in the magnetic circuit and provided with a gear wheel 136 which meshes with a driving gear wheel 137 fitted on an axle 138 furnished with a handle 139 by which the bushing 135 can be rotated. The high-frequency transducer with an adjustable pitch comprises a bearing plate 140 rigidly secured to the bushing 135, said plate 140 mounting a flat multi-link parallelogram mechanism 141. The flat multi-link parallelo-gram mechanism is made so that its first joint 142 is firmly fastened on the plate 140 and the last joint 143 has a nut 144 secured thereto and provided with a screw 145. The screw 145 with the nut 144, which are the opening drive, are intended to open the parallelogram mechanism 141. The second end of the screw 145 is fitted in a bearing placed at the first joint 142 and fixed by longitudinal movement. A gear wheel 146 is rigidly mounted on the screw 145 and meshes with a wheel 147 fitted on an axle 148 placed in the bushing 135 and equipped with a handle 149. Rotation of the handle 149 through the engaged wheels 147 and 146, the screw 145, the nut 144 can move the joint 143 with respect to the joint 142, the distances between intermediate joints 150, 151, 152 change but remain equal to one another. To prevent end plays in the parallelogram mechanism 141 in the direction of axles of the joints 150, 151, 152 the multi-link parallelogram mechanism is pressed against the plate 140 by braces 153, which carry a hinged housing 154 containing a discrete flat radiator made as packed L-shaped plates 155. The butts 156 of these plates 155 mount sections 157 of the windings of the high-frequency transducer. The winding sections 157 can either be secured by fitting in slots of butts of the plates 155 or by glue, when miniaturization requires this. Each plate is connected to a respective joint by pins. The plates located under the pin-tied plate are provided with slots, which are no obstacle to plates shifting with respect to one another. Such coupling allows permanent and simultaneous change of pitch between the sections of the high-frequency transducer during opening the parallelogram mechanism. The pitch is an important parameter of a high-frequency transducer in excitation of plate waves in sheets and has a direct effect on the wavelength and selection of a respective frequency of excited ultrasonic vibrations.

The device is operated as follows. The device is set on the sheet to be tested, the coil 134 of the magnetizing device is cut in, high-frequency voltage is supplied to the sections 157 of the high-frequency transducer. Depending on the type of plate waves to be excited in the sheet the angle between the directions of the magnetizing field and the radiation direction is adjusted by the handle 139.

The plate 140 rotates about the bushing 135 together with the parallelogram mechanism 141 mounted thereon and the set of L-shaped plates 155, which butts 156 with the winding sections 157 fitted therein form the periodic structure of the high-frequency transducer. When longitudinal plate waves are used, the angle between the radiation direction, which coincides with the normal to the direction of the section 157, and the direction of the magnetization field, which coincides with the line connecting the pole shoes 158, 159, should be zero. When transverse plate waves are employed, this angle is selected within the 10° – 60° range in accordance with the above described method for excitation and detection of plate waves depending on the magnetic properties of the material to be tested. Adjustment of the angle is done by the handle 139. The pitch between the sections 157 of the high-frequency transducer is adjusted by the handle 149. Rotation is transmitted to the bevel gear wheel 147, the wheel 146, the screw 145. When the screw 145 rotates, the nut 144 moves along the screw separating the joints of the multi-link parallelogram mechanism 141 with the joints 143, 150, 151, 152, which shift the L-shaped plates 155 one with respect to another so that the pitch between the sections 157 changes simultaneously. The change in the pitch between the sections 157 and in the operational frequency brings about a change in the ultrasonic plate waves excited in the sheet. The remaining part of the device operation is similar to the operation of already described methods and devices. It should be noted that placing the high-frequency transducer in one casing with the magnetizing device is not obligatory and in automatic apparatuses there can be used a device comprising adjustment of one parameter, that is the adjustment of the pitch between the winding sections of the high-frequency transducer.

Figure 45:
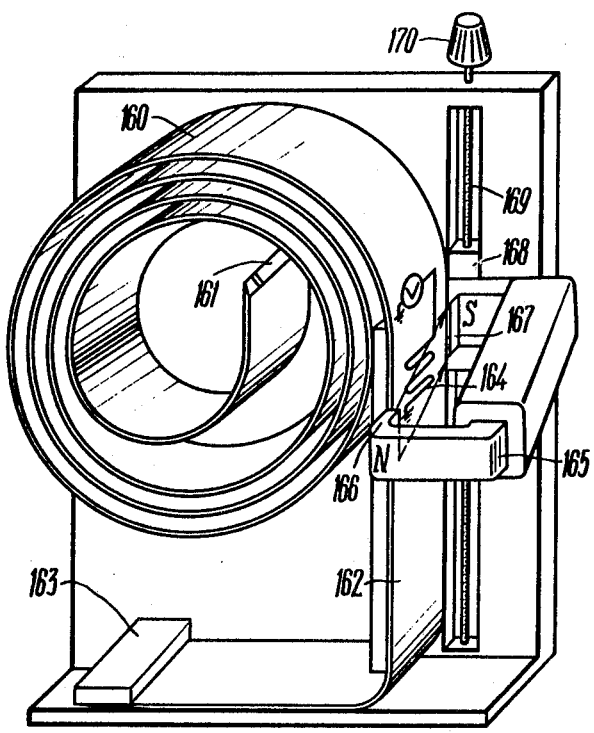
FIG. 45 shows an ultrasonic delay line with a transmitting piezoelectric transducer and receiving electromagnetic acoustical transducer.

Realization of the proposed method for excitation and detection of ultrasonic plate waves permits development of an ultrasonic delay line (FIG. 45) employing transverse plate waves and comprising an acoustic guide 160, made as a band from nonretentive material. A transmitting transducer 161 is rigidly secured at one end of the band and sound dampers are fitted on the sides (not shown in FIG. 45). The acoustic guide 160 is made as a spiral provided with a straight portion 162. A sound damper 163 is installed at the other end of the acoustic guide 160. The straight portion 162 carries a receiving transducer 164 with a magnetizing device 165 comprising a magnetic circuit equipped with pole shoes 166 and 167 arranged in the direction of the side edges of the straight portion 162 of the acoustic guide. The pole shoes 166 and 167 are displaced along the length of the straight portion 162 of the acoustic guide 160 so that the magnetizing field makes an angle with the longitudinal axis of the guide 160, which is selected from the 10° to 60° range depending on the properties of the material of the acoustic guide 160 in accordance with the above described method for excitation and detection of transverse plate waves.

The high-frequency transducer 164 rigidly connected to the magnetizing device 165 is positioned on the straight portion 162 of the acoustic guide 160 in the zone of the magnetizing field. The direction of propagation of ultrasonic vibrations of the transducer 164 coincides with the direction of the axis of the acoustic guide 160. A weakly focused high-frequency transducer can also be employed in the device. In this case the symmetry axis of the transducer should coincide with the direction of the acoustic guide.

The magnetizing device 165 with the high-frequency transducer 164 are mounted on a carriage provided with a drive screw 169 with a handle 170 attached to its end. In the process of adjustment the delay time is regulated by means of the handle 170 of the screw 169. When a line has several outlets, it comprises several receiving transducers with magnetizing devices installed at the outlet straight portion 162 of the acoustic guide 160 and provided with independent drives for movement along the outlet portion of the acoustic guide. Such design of the delay line allows reception of one pulse with a different time delay.

The ultrasonic delay line operates as follows. The transmitting transducer 161, which is for example an Y-cut piezoplate, excites in the acoustic guide 160 a pulse of a transverse plate wave, which propagates along the acoustic guide 160 at the velocity of the $SS_o$ mode of the transverse wave. The advantage of this type of waves consists in weak dispersion effect (for $SS_o$ mode) and, consequently, insignificant attenuation of the signal amplitude and distortion of its shape. When the pulse reaches the portion of the acoustic guide 160, over which the receiving transducer 164 with the magnetizing device 165 are positioned, it is received and passed over to the processing circuit (not shown). The parameters of the receiving transducer (pitch $\lambda$ and the angle between the direction of the transducer detection and the vector $\alpha$ of the magnetizing device) are preselected, because the operational frequency of the ultrasonic delay line is known, in accordance with the procedure outlined in the description of the method for excitation and detection of transverse plate waves.

The sound damper 163 is set up at the end of the acoustic guide 160 to eliminate false signals. The delay can be changed by moving the magnetizing device 165 with the receiving transducer 164 along the straight portion 162 of the acoustic guide 160. A delay scale can be marked on the handle 170 of the drive. Several receiving transducers with independent or dependent delay control can be positioned on the straight portion 162 of the acoustic guide 160 for obtaining various delays.

It is evident that a variety of alternative embodiments can be realized within the scope of this invention. The above described method can be employed for excitation of other types of waves propagating in waveguides, e.g. Love waves. It is to be understood that the above described embodiments are illustrative of the principle of the invention and not to be taken by way of limitation of the scope of this invention.

What is claimed is:

1. A method of excitation and reception of ultrasonic plate waves in a workpiece comprising generating a high-frequency electromagnetic field acting on the surface of the workpiece by a transducer consisting of a system of flat radiators forming a comb-like structure positioned discretely in the direction of radiation with a pitch divisible by the wavelength; applying a magnetizing field to the workpiece whose vector is parallel to the surface of the workpiece in the area of the high-frequency electromagnetic field, and orienting the vector of the magnetizing field for exciting transverse (shear) plate waves with respect to the transducer of flat radiators at an angle $\alpha$ relative to the direction of radiation, wherein $|\alpha| > 0$.

2. A method as claimed in claim 1, wherein, when said transverse normal waves are excited in carbon steel workpieces, the vector of the magnetizing field is oriented with respect to said system of flat radiators at an angle $\alpha$ within a range of $\pm(10° \text{ to } 60°)$ relative to the direction of radiation.

3. A method as claimed in claim 1, wherein, when said normal waves are excited in workpieces from non-retentive materials, the vector of the magnetizing field is oriented with respect to the system of flat radiators at an angle $\alpha$ within a range of $\pm(20° \text{ to } 90°)$ relative to the direction of radiation.

4. A method as claimed in claim 1, wherein with separate excitation and reception of plate waves the pitch between the flat radiators ensuring the reception of normal waves is determined considering the effect of dispersion distortions on the specified test base by measuring the mean wavelength in a pulse of normal waves by superposition method.

5. A method of excitation and reception of ultrasonic plate waves in a workpiece comprising generating a high-frequency electromagnetic field acting on the surface of the workpiece by a transducer consisting of a system of flat radiators forming a comb-like structure and positioned discretely in the direction of radiation with a pitch divisible by the wavelength; applying a magnetizing field to the workpiece whose vector is parallel to the surface of the test workpiece in the area of the high-frequency electromagnetic field; orienting the vector of the magnetizing field for exciting transverse (shear) plate waves with respect to the transducer of flat radiators at an angle $\alpha$ relative to the direction of radiation, and exciting longitudinal plate waves for simultaneous excitation and reception of pulses of transverse and longitudinal plate waves by selecting at least two excitation frequencies of the high-frequency electromagnetic field wherein the wavelengths of the transverse and longitudinal plate waves are equal according to the formula $$f_1 = c_{x1}/\lambda_1, f_2 = c_{x2}/\lambda_2$$

where $c_{x1}$ and $c_{x2}$ are phase velocities of transverse and longitudinal plate waves, respectively, and $\lambda_1$ and $\lambda_2$ are the lengths of transverse and longitudinal plate waves, respectively, the pitch between the flat radiators being determined according to the formula $$t = \lambda_1 = \lambda_2.$$

6. A method as claimed in claim 5, wherein for simultaneous excitation and reception of pulses of transverse and longitudinal plate waves with equal amplitudes on a specified test base, the vector of the magnetization field is oriented with respect to the system of flat radiators at an angle $\alpha$ within the range of $\pm(5° \text{ to } 40°)$ relative to the direction of radiation.

7. A method as claimed in claim 5, wherein for simultaneous excitation and reception of pulses of transverse and longitudinal plate waves focused in a specified point, the vector of a magnetization field is oriented with respect to a system of curved flat radiators at an angle $\alpha$ within the range of $\pm(0° \text{ to } 60°)$ relative to the direction of radiation.

8. A method as claimed in claim 5, wherein for a minimum test base of the workpiece is selected from the condition:

$$L \gtrsim \frac{\tau}{2} \cdot \frac{C_{y\,max} \cdot C_{y\,min}}{C_{y\,max} - C_{y\,min}}$$

where $\tau$ is the duration of the received pulse of a normal wave;

$C_{y\,max}$, $C_{y\,min}$ are group velocities of transverse and longitudinal waves.

9. A method as claimed in claim 5, wherein for excitation of a longitudinal plate wave (Lamb wave) focused in a specified point, the vector of the magnetizing field is oriented with respect to the system of flat radiators, by forming said radiators along curves with radii equal to the distance to the focusing point, their length being equal to the effective width of the magnetizing field so that its direction coincides with the radiation direction.

10. A method as claimed in claim 5, wherein with separate excitation and reception of normal waves the pitch between the flat radiators ensuring reception of normal waves is determined considering the effect of dispersion distortions on the specified test base by measuring the mean wavelength in a pulse of plate waves by superposition method.

11. A device for excitation and reception of ultrasonic plate waves in workpieces, e.g. in sheets, comprising: a foundation; a magnetizing device mounted on said foundation so that it can turn in a plane parallel to the surface of the workpiece; a bracket secured on said foundation so that the workpiece is between said foundation and said magnetizing device, a lever mechanism with a lifting means connecting said bracket to said foundation; a frame secured to said lever mechanism; lever means secured on said frame; a system of flat radiators constituting a high-frequency transducer secured on said bracket by means of said lever means and pressed against the workpiece by said lever means; said high-frequency transducer being positioned coaxially with said magnetizing device; a protective device enveloping said high-frequency transducer and placed on said frame; said protective device including at least two rollers mounted in one plane and having parallel axles with an elastic electrically strong and mechanically durable ring band secured thereon and moving at the speed of the workpiece, and a layer of material covering a portion of said rollers, which is in contact with the workpiece, said layer of material ensuring reliable coupling of said rollers with the surface of the workpiece.

12. A device as claimed in claim 11, wherein said magnetizing device comprises a solenoid, whose axis is parallel to the surface of the workpiece, and means for turning and fixing the solenoid in positions corresponding to excitation of required ultrasonic normal waves.

13. A device for excitation and reception of ultrasonic plate waves in workpieces (e.g. in sheets) comprising: two guides positioned along a workpiece; a platform, which is able to move with respect to the workpiece and is placed on one of said guides; a bracket mounted on said one guide and having a respective guide placed across the test workpiece and resting on said other guide placed along the workpiece; a carriage with a drive means, which is positioned on said guide of said bracket; an electric drive means mounted on said carriage; a magnetizing device with a lifting device means and a lever securing the lifting drive means on said carriage; lever means positioned on said magnetizing device; a high-frequency transducer mounted on said magnetizing device by said lever means so that the transducer can turn about an axis normal to the surface of the workpiece; said high-frequency transducer being pressed against the surface of the workpiece by said lever means; at least two welded seam position sensors mechanically connected to said high-frequency transducer; at least two electromagnetic holder means mechanically connected to said high-frequency transducer; said welded seam position sensors and said electromagnetic holder means being positioned in pairs over the edges of the workpiece for ensuring travelling of the platform with the workpiece and travelling of the high-frequency transducer along the workpiece welded seam under test by said electric drive means.

14. A device as claimed in claim 13, comprising means whereby said bracket with its guide is placed on the platform so that it can rotate and is spring-loaded in the direction of movement of the test workpiece, whereas the platform includes an electromagnetic holder means for holding the platform with respect to the longitudinal guide and electric return drives to bring said high-frequency transducer with said magnetizing device to the initial position.

15. A device for excitation and reception of normal waves in workpieces, e.g. pipes, comprising: a vertical guide bearing with a screw drive; a movable bracket mounted on said vertical guide bearing and able to move therealong; lever means including a lifting drive secured on said movable bracket; guiding rollers in contact with the workpiece; a magnetizing device mounted on said guiding rollers and secured by the lever means on said movable bracket; said magnetizing device being constituted as a sectionalized S-shaped magnetic circuit including at least three pole shoes with a stationary central pole shoe which is interchangeable, and two other adjustable pole shoes assembled of plates oriented with respect to the axis of the test workpiece, means for moving said plates along the S-shaped magnetic circuit including screw pairs and an adjusting and fixing means to assume the shape of the surface of the workpiece under test; at least two high-frequency transducers permanently pressed against the surface of the workpiece and able to move on said magnetizing device; said high-frequency transducers being positioned symmetrically with respect to the longitudinal axis of said S-shaped magnetic circuit, and means for moving said high frequency transducers along said S-shaped magnetic circuit including screw pairs secured so that the transducers can rotate about a vertical axis in a plane parallel to the surface of the workpiece.

16. A device as claimed in claim 15, comprising means whereby said adjustable pole shoes of the S-shaped magnetic circuit can rotate around axes which coincide with the axis of the S-shaped magnetic circuit.

17. A device as claimed in claim 15, comprising a casing for the high-frequency transducer including a base made of material with a low melting point and assuming the shape of the surface of the workpiece under test by deforming when heated.

18. A device for excitation and reception of plate waves in workpieces, comprising: a magnetizing device constituted as a sectionalized magnetic circuit with two pole shoes travelling individually across and along the workpiece; means including screw drives for displacing said pole shoes along the workpiece and for fixing said shoes in definite positions; a bracket positioned on one of said pole shoes; a guide mounted in said bracket; a spring-loaded lever means mounted on said guide; a high-frequency transducer mounted on said lever means so that it can be moved along the workpiece and a frame supporting said transducer and including an elastic base assuming the shape of the workpiece surface when pressed thereto by said lever means.

19. A device for excitation and reception of plate waves in workpieces, comprising: a magnetizing device with a hand drive; a high-frequency transducer mounted on said hand drive of the magnetizing device and provided with plate, a multi-link parallelogram mechanism with a separate drive installed on said plate; a discrete flat radiator constituted by a plurality of sections; L-shaped plates assembled as a pack, each of said L-shaped plates being hinged to respective links of the parallelogram mechanism and having remote ends, said flat sections of the radiator being mounted on the ends of the L-shaped plates.

20. An ultrasonic delay line for excitation and reception of transverse normal waves, comprising: an acoustic guide made as a piece of band of a ferromagnetic material and having two ends; said guide having side edges and including a covering of sound-proof material on said side edges; a radiator positioned on one end of said acoustic guide; the second end of the guide having a straight portion; a casing placed on the straight portion of the second end of said acoustic guide and provided with screw drive means for travelling along said straight portion of the acoustic guide; a receiving transducer constituted as a high-frequency transducer positioned in said casing; and a magnetizing device positioned in said casing.

21. An ultrasonic delay line as claimed in claim 20, wherein a plurality of said high-frequency transducers with magnetizing devices are provided with individual drive means for travelling along said acoustic guide.

* * * * *